(12) United States Patent
Harrison et al.

(10) Patent No.: US 7,622,310 B2
(45) Date of Patent: Nov. 24, 2009

(54) CONTAMINATION MONITORING AND CONTROL TECHNIQUES FOR USE WITH AN OPTICAL METROLOGY INSTRUMENT

(75) Inventors: Dale A. Harrison, Austin, TX (US); Matthew Weldon, Austin, TX (US)

(73) Assignee: Metrosol, Inc., Austin, TX (US)

( * ) Notice: Subject to any disclaimer, the term of this patent is extended or adjusted under 35 U.S.C. 154(b) by 179 days.

(21) Appl. No.: 11/600,414

(22) Filed: Nov. 16, 2006

(65) Prior Publication Data
US 2008/0073560 A1 Mar. 27, 2008

Related U.S. Application Data

(60) Provisional application No. 60/795,467, filed on Apr. 27, 2006.

(51) Int. Cl.
*H01L 21/66* (2006.01)

(52) U.S. Cl. ...................................................... 438/14

(58) Field of Classification Search ....................... None
See application file for complete search history.

(56) References Cited

U.S. PATENT DOCUMENTS

| | | | |
|---|---|---|---|
| 5,344,522 A | 9/1994 | Yagi et al. | |
| 5,510,624 A | 4/1996 | Zaluzec | |
| 5,565,038 A * | 10/1996 | Ashley ........................ | 134/2 |
| 5,584,963 A | 12/1996 | Takahashi | |
| 5,669,979 A | 9/1997 | Elliott et al. | |
| 5,814,156 A | 9/1998 | Elliott et al. | |
| 6,015,759 A | 1/2000 | Khan et al. | |
| 6,165,273 A | 12/2000 | Fayfield et al. | |
| 6,261,853 B1 | 7/2001 | Howell et al. | |
| 6,274,874 B1 | 8/2001 | Sidhu | |
| 6,288,769 B1 | 9/2001 | Akagawa et al. | |
| 6,387,602 B1 | 5/2002 | Hayden et al. | |
| 6,403,966 B1 | 6/2002 | Oka | |
| 6,433,877 B2 | 8/2002 | Watanabe et al. | |
| 6,490,305 B2 | 12/2002 | Govorkov et al. | |
| 6,519,045 B2 | 2/2003 | Kwon | |
| 6,714,300 B1 | 3/2004 | Rosenewaig et al. | |
| 6,724,460 B2 | 4/2004 | Van Schaik et al. | |
| 6,726,886 B2 | 4/2004 | Shiramizu et al. | |
| 6,740,247 B1 | 5/2004 | Han et al. | |
| 6,813,026 B2 | 11/2004 | McAninch | |
| 6,891,627 B1 * | 5/2005 | Levy et al. ................... | 356/625 |

(Continued)

OTHER PUBLICATIONS

Search Report, PCT/US07/06765, Mar. 11, 2008, 2 pgs.

(Continued)

*Primary Examiner*—Charles D. Garber
*Assistant Examiner*—Andre' C Stevenson
(74) *Attorney, Agent, or Firm*—O'Keefe, Egan, Peterman & Enders LLP

(57) ABSTRACT

A technique is provided for generating and subsequently monitoring the controlled environment(s) within an optical metrology instrument in such a manner as to minimize absorbing species within the light path of the metrology instrument and to minimize the build-up of contaminants on the surfaces of optical elements that may result in performance degradation. Both evacuation and backfill techniques may be utilized together along with a monitoring technique to determine if the environmental is suitable for measurements or if the environment should be regenerated. The optical metrology instrument may be an instrument which operates at wavelengths that include vacuum ultra-violet (VUV) wavelengths.

67 Claims, 10 Drawing Sheets

U.S. PATENT DOCUMENTS

| | | |
|---|---|---|
| 6,907,058 B2 | 6/2005 | Vogler et al. |
| 6,914,208 B2 | 7/2005 | Shimizu et al. |
| 6,930,771 B2 | 8/2005 | Rosenewaig et al. |
| 7,006,222 B2 | 2/2006 | Krishnan |
| 7,067,818 B2 | 6/2006 | Harrison |
| 7,068,370 B2 | 6/2006 | Rosenewaig et al. |
| 7,126,131 B2 | 10/2006 | Harrison |
| 7,202,951 B1 | 4/2007 | Janik et al. |
| 7,253,901 B2 | 8/2007 | Janik et al. |
| 2003/0231302 A1* | 12/2003 | Hunt ........................ 356/237.2 |
| 2004/0150820 A1 | 8/2004 | Nikoonahad et al. |
| 2004/0165165 A1 | 8/2004 | Yun et al. |
| 2005/0072943 A1 | 4/2005 | Yamanaka et al. |
| 2005/0117226 A1 | 6/2005 | Yamamoto |
| 2005/0231719 A1 | 10/2005 | Rosenewaig et al. |
| 2006/0228897 A1* | 10/2006 | Timans ........................ 438/758 |

OTHER PUBLICATIONS

Copending Application, "Contamination Monitoring And Control Techniques For Use With An Optical Metrology Instrument", U.S. Appl. No. 11/600,477, filed Nov. 16, 2006, 53 pgs.

Copending Application, "Contamination Monitoring And Control Techniques For Use With An Optical Metrology Instrument", U.S. Appl. No. 11/600,413, filed Nov. 16, 2006, .54 pgs.

Okoroanyanwu et al., "Contamination Monitoring And Control On ASML MS-BII 157Nm Exposure Tool", AMD, California, IMEC, Belgium, 2004, 13 pgs.

Kunz et al., "Experimentation And Modeling Of Organic Photocontamination On Lithographic Optics", J. Vac., Sci. Technology, B18(3), May/Jun. 2000, pp. 1306-1313.

* cited by examiner

CONTAMINATION MONITORING AND CONTROL TECHNIQUES FOR USE WITH AN OPTICAL METROLOGY INSTRUMENT

RELATED APPLICATIONS

The present application claims priority to U.S. Provisional Patent Application No. 60/795,467 filed Apr. 27, 2006, the disclosure of which is expressly incorporated herein by reference. The present application also expressly incorporates by reference the following two U.S. patent applications concurrently filed on the same date as the present application: U.S. patent application Ser. No. 11/600,414, entitled CONTAMINATION MONITORING AND CONTROL TECHNIQUES FOR USE WITH AN OPTICAL METROLOGY INSTRUMENT by Harrison and Weldon; and U.S. patent application Ser. No. 11/600,477, entitled CONTAMINATION MONITORING AND CONTROL TECHNIQUES FOR USE WITH AN OPTICAL METROLOGY INSTRUMENT by Harrison and Weldon.

BACKGROUND OF THE INVENTION

The present application relates to the field of optical metrology and more particularly to optical metrology that may be performed in the vacuum ultraviolet (VUV).

In one embodiment, a means by which accurate and repeatable optical metrology may be performed in the vacuum ultraviolet (VUV) is provided. In one embodiment, the technique disclosed herein can be used to ensure that vacuum ultraviolet reflectometers generate highly stable and repeatable results in the presence of both gaseous and surface contaminants. In another embodiment, the techniques disclosed herein provide a means for obtaining accurate reflectance data from samples whose surfaces themselves may be contaminated.

Optical metrology techniques have long been employed in process control applications in the semiconductor manufacturing industry due to their non-contact, non-destructive and generally high-throughput nature. The vast majority of these tools operate in some portion of the spectral region spanning the deep ultraviolet to near-infrared wavelengths (DUV-NIR generally 200-1000 nm). The continuous push towards developing smaller devices comprised of thinner layers has challenged the sensitivity of such instrumentation. An effort to develop optical metrology equipment utilizing shorter wavelengths (below 200nm), where greater sensitivity to subtle changes in processing conditions can be realized has been considered. Approaches to performing optical measurements at shorter wavelengths such as a system and method for a vacuum ultraviolet (VUV) reflectometer are described in U.S. application Ser. No. 10/668,642, filed on Sep. 23, 2003, now U.S. Pat. No. 7,067,818 and U.S. application Ser. No. 10/909,126, filed on Jul. 30, 2004, now U.S. Pat. No. 7,126,131 the disclosures of which are both expressly incorporated herein by reference.

Contamination of optical surfaces like windows and mirrors is a serious impediment to the operation of optical instruments in the VUV. Moisture and residual molecules, particularly hydrocarbon compounds, may deposit on such surfaces over time dramatically reducing their performance. These effects have formed the focus of previous investigations owing to their impact on the design, development and performance of 193 and 157 nm lithographic exposure tools.

In order to ensure the tremendous sensitivity enhancements theoretically offered by VUV optical metrology instruments are practically realized, it would be highly desirable to develop an instrument with the inherent capability of reducing, removing or altogether eliminating the build up of contaminates on its optical surfaces. Furthermore, if this self-cleaning capability could be realized without the addition of potentially expensive and complicated components it would represent a great benefit to tool owners.

When present on the surfaces of samples under investigation, contaminate layers may significantly contribute to measured optical responses in the VUV yielding inaccurate and/or erroneous results. These effects are of particular concern when the samples are comprised of ultra thin films (<100 Å), whose thicknesses may themselves be comparable to the thicknesses of the contaminate layers.

One technique contemplated for improving the measurement of semiconductor wafers by removing contamination layers in a cleaning step includes employing microwave radiation and/or radiant heating, prior to measurement. Although enhanced measurement repeatability is reported using this approach, the method requires that a separate cleaning system be coupled to an existing measurement system resulting in increased system cost and design complexity.

In light of these disadvantages it would be desirable to develop a measurement system that was itself capable of removing contaminants from the surface of samples, so as to ensure accurate and highly repeatable results were achieved. Such an instrument would be capable of simultaneously cleaning and measuring specific locations on the sample without requiring additional components, above and beyond those normally required for measurement, thereby reducing system cost and design complexity. Furthermore, such an instrument would not require alignment of separate cleaning and measurement subsystems. In addition, such an instrument would avoid needlessly "cleaning" the entire sample, while at the same time ensuring that consistent cleaning results were obtained at all measurement locations.

SUMMARY OF THE INVENTION

One embodiment of the disclosed techniques provides a technique for generating and subsequently monitoring the controlled environment(s) within a VUV optical metrology instrument in such a manner as to minimize, or all together eliminate, the build-up of contaminants on the surfaces of optical elements that may result in performance degradation.

Another embodiment discloses a technique for reducing surface contaminants from optical elements contained within the optical path (or sub-path) of an optical metrology instrument. The technique may be utilized in one embodiment in such a manner as to not require that additional components and/or instrumentation be coupled to, or integrated into, existing metrology equipment.

Another embodiment discloses a technique whereby surface contaminants on optical elements within an optical metrology instrument are monitored so that cleaning procedures can be performed as deemed necessary. The technique may further enable separate optical paths of the instrument to be monitored, and subsequently cleaned, independent of one another.

In yet another embodiment, a technique is disclosed for removing contaminants from the surface of a sample prior to recording an optical response from said sample in order to ensure that accurate results are obtained. In one alternative, the technique may be implemented in such a manner as to not require that additional components and/or instrumentation be coupled to, or integrated into, existing metrology equipment.

In yet another embodiment, a technique is disclosed for characterizing contaminants on the surface of a sample. In addition to providing insight into the nature of the contaminant itself, the technique also provides a means by which accurate sample measurements can be performed in light of contamination layers which may be present on their surfaces.

In another embodiment, a method of controlling an atmosphere in an optical metrology tool is provided. The method may include providing at least a first environmentally controlled chamber and a second environmentally controlled chamber, the first and second environmentally controlled chambers configured for passage of a light beam having wavelengths below DUV wavelengths. The method may further include lowering the concentration of an optical absorbing species in at least one of the first and second environmentally controlled chambers by utilizing vacuum evacuation techniques, the at least one of the first and second environmentally controlled chambers being a controlled atmosphere chamber. Further the method may include backfilling, with a non-absorbing gas, the controlled atmosphere chamber so as to improve optical performance by increasing a pressure within the controlled atmosphere chamber above a vacuum evacuation pressure level and transmitting the light beam having wavelengths below DUV wavelengths while the controlled atmosphere chamber is in the backfilled state.

Another embodiment includes a method of controlling an atmosphere in an optical metrology tool that may comprise providing at least an environmentally controlled sample chamber and an environmentally controlled optics chamber, the sample chamber and optics chamber each being configured for passage of a light beam having wavelengths below DUV wavelengths. The method may further comprise decreasing from an ambient state the concentration of moisture or oxygen in at least one of the sample chamber and the optics chamber by utilizing vacuum evacuation techniques, the at least one of the sample chamber and the optics chamber in which the decreasing occurs being a controlled atmosphere chamber. The method may also include backfilling, with a VUV non-absorbing gas, the controlled atmosphere chamber so as to decrease contaminant migration by increasing a pressure within the controlled atmosphere chamber above a vacuum evacuation pressure level and transmitting the light beam having wavelengths below DUV wavelengths while the controlled atmosphere chamber is in the backfilled state.

In another embodiment a method of controlling an atmosphere in an optical metrology tool may include providing at least an environmentally controlled sample chamber and an environmentally controlled optics chamber, the sample chamber and optics chamber each being configured for passage of a light beam having wavelengths below DUV wavelengths. The method may further include providing a sample beam optical path and a reference beam optical path, the optical path lengths of the sample beam optical path and the reference beam optical patch being matched. The method also may include decreasing from an ambient state the concentration of moisture or oxygen in at least one of the sample chamber and the optics chamber by utilizing vacuum evacuation techniques, the at least one of the sample chamber and the optics chamber in which the decreasing occurs being a controlled atmosphere chamber. The method may further include backfilling, with a VUV non-absorbing gas, the controlled atmosphere chamber so as to improve the optical performance by increasing a pressure within the controlled atmosphere chamber above a vacuum evacuation pressure level and transmitting the light beam having wavelengths below DUV wavelengths while the controlled atmosphere chamber is in the backfilled state.

In another embodiment, a method of determining an environmental contamination state in an optical metrology tool is provided. The method may include obtaining a first intensity measurement from a reference sample at a first time and obtaining a second intensity measurement from the reference sample at a second time. Further, the method may include analyzing the first and second intensity measurements and determining from the analyzing of the first and second intensity measurements if the environmental contamination state of the optical metrology tool is suitable for further use based upon variations between the first intensity and the second intensity.

In another embodiment, a method of determining an environmental contamination state in an optical metrology tool that operates at wavelengths that at least include wavelengths below DUV wavelengths is provided. The method may include obtaining a first intensity spectrum measurement from a reference sample at a first time, the first intensity spectrum measurement comprising at least a plurality of wavelengths below DUV wavelengths and obtaining a second intensity measurement from the reference sample at a second time, the first intensity spectrum measurement comprising at least a plurality of wavelengths below DUV wavelengths. The method may further include analyzing the first and second intensity measurements and determining from the analyzing of the first and second intensity measurements if the environmental contamination state of the optical metrology tool is suitable for further use based upon variations between the first intensity and the second intensity.

A further understanding of the nature of the advantages of the concepts disclosed herein may be realized following review of the following descriptions and associated drawings.

BRIEF DESCRIPTION OF THE DRAWINGS

A more complete understanding of the present invention and advantages thereof may be acquired by referring to the following description taken in conjunction with the accompanying drawings, in which like reference numbers indicate like features. It is to be noted, however, that the accompanying drawings illustrate only exemplary embodiments of the invention and are therefore not to be considered limiting of its scope, for the invention may admit to other equally effective embodiments.

DESCRIPTION OF THE PREFERRED EMBODIMENTS

Figure 1:
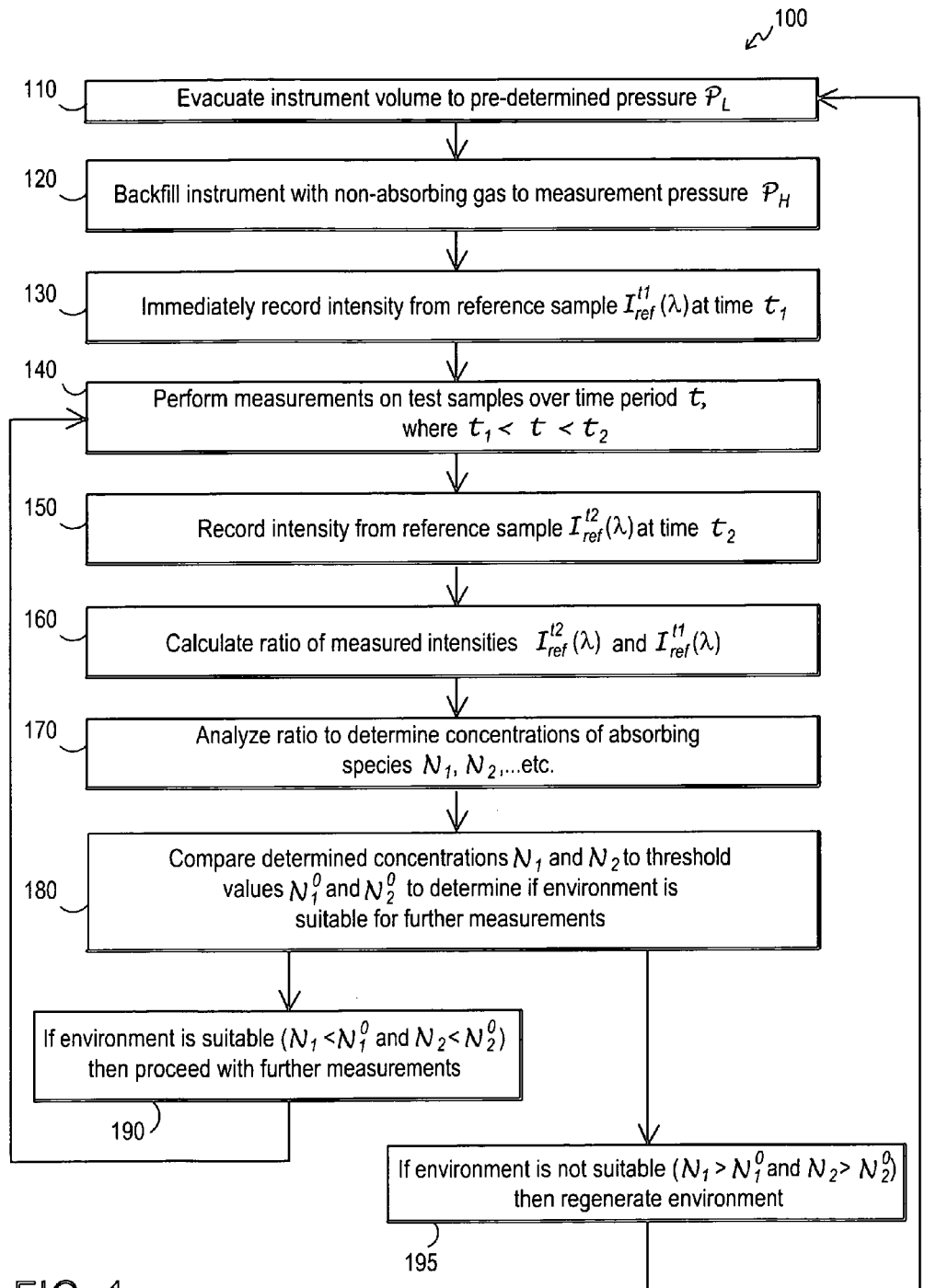
FIG. 1 is an exemplary environmental monitoring flowchart.

To enhance the sensitivity of optical metrology equipment for challenging applications it is desirable to extend the range of wavelengths over which such measurements are performed. Specifically, it is advantageous to utilize shorter wavelength (higher energy) photons extending into, and beyond, the region of the electromagnetic spectrum referred to as the vacuum ultra-violet (VUV). Vacuum ultra-violet (VUV) wavelengths are generally considered to be wavelengths less than deep ultra-violet (DUV) wavelengths, i.e. less than about 190 nm. While there is no universal cutoff for the bottom end of the VUV range, some in the field may consider VUV to terminate and an extreme ultra-violet (EUV) range to begin (for example some may define wavelengths less than 100 nm as EUV). Though the principles described herein may be applicable to wavelengths above 100 nm, such principles are generally also applicable to wavelengths below 100 nm. Thus, as used herein it will be recognized that the term VUV is meant to indicate wavelengths generally less than about 190 nm however VUV is not meant to exclude lower wavelengths. Thus as described herein VUV is generally meant to encompass wavelengths generally less than about 190 nm without a low end wavelength exclusion. Furthermore, low end VUV may be construed generally as wavelengths below about 140 nm.

It is generally true that virtually all forms of matter (solids, liquids and gases) exhibit increasingly strong optical absorption characteristics at VUV wavelengths. In part, it is this rather fundamental property of matter which is itself responsible for the increased sensitivity available to VUV optical metrology techniques. This follows as small changes in process conditions, producing undetectable changes in the optical behavior of materials at longer wavelengths, can induce substantial and easily detectable changes in the measurable characteristics of such materials at VUV wavelengths. This highly non-linear dependence of photon absorption cross section on wavelength presents tremendous opportunities for VUV optical metrology instrumentation; unfortunately it also introduces associated complications.

One such complication relates to the fact that VUV radiation can not propagate through standard atmospheric conditions. VUV photons are strongly absorbed by $O_2$ and $H_2O$ and hence, these species must be maintained at sufficiently low levels (for example typically sub-PPM) so as to permit transmission along the optical path of metrology instrumentation. To this end vacuum or purge methods, using a non-absorbing purge gas (like nitrogen, argon or helium), are typically employed. Purge methods can be reasonably effective at lowering the concentration of gaseous $O_2$ and $H_2O$, but it is very difficult to remove adsorbed water in a timely fashion without employing vacuum techniques. Vacuum methods, though more efficient at removing adsorbed $H_2O$, inadvertently promote surface contaminant migration as a consequence of the increase in mean free path experienced by such species at reduced pressure.

In light of these disparate considerations, it follows that neither vacuum nor purge methods alone constitute the most effective means of generating, and subsequently maintaining, the controlled environment required to perform optical measurements in the VUV. Rather, it is desirable to utilize a procedure which combines elements of both techniques in order to ensure optimum tool performance. In short, vacuum is initially employed to quickly lower the concentration of moisture and oxygen species to acceptable levels, following which the pressure within the instrument is back filled with a non-absorbing gas.

In one embodiment, in order to lower the concentration of adsorbed moisture to an acceptable level it is typically desirable to lower the pressure in the tool to somewhere in the vicinity of $1\times10^{-5}$-$1\times10^{-6}$ Torr. Care may be taken to ensure the optical surfaces of the instrument are not exposed to VUV radiation during this time since this may lead to the formation of photo-deposited contaminant layers. This situation is readily avoided by either shuttering or powering off VUV sources prior to evacuation.

The time required to achieve the requisite vacuum condition depends on many aspects of the system (i.e. temperature, internal surface area of instrumental volume, pumping speed of vacuum system, etc.) but will be largely driven by exposure of internal surfaces to ambient air during the sample load process. As such, it follows that system pump-down time will be minimized through intelligent use of load-lock mechanisms; thereby increasing system throughput and reducing the migration of contaminates.

The pump-down cycle time can also be shortened by applying energy to the adsorbed water bed through mechanical, thermal or radiative methods. Mechanical energy can be applied during the initial portion of the pump down cycle by bleeding in controlled purge gas. Thermal energy can be applied by heating the walls of the instrument, however this approach could promote contaminate migration and introduce mechanical instabilities. UV lamps can also be used to transfer energy directly to adsorbed water molecules, but may simultaneously result in contaminant photo-deposition.

Once the concentration of absorbing species within the instrumental volume is sufficiently lowered, the controlled environment required to support operation (i.e. permit sufficient transmission of VUV photons) is achieved by back filling the volume of the instrument with a high-purity non-absorbing gas. While contamination considerations may encourage maintaining the pressure of the instrument at elevated levels, mechanical considerations generally limit practical operating pressures to somewhere in the neighborhood of atmospheric conditions. Consequently, pressures in the range of 300-700 Torr are typically employed. Thus optical performance may be improved by increasing optical transmission. The optical transmission may be increased by lowering the oxygen and/or moisture content through the use of vacuum techniques. In addition, optical performance may also be increased by suppressing the migration of absorbing species (i.e. contaminants) from surfaces through the use of backfill techniques. Adsorbing contaminants which migrate from instrument surfaces and adhere to optical surfaces can significantly degrade the performance of such elements, resulting in mirrors with reduced reflectivity and windows with decreased transmission characteristics.

Over time the quality of the controlled environment within the instrument can be expected to degrade due to a variety of sources; including but not limited to outgassing from interior surfaces, permeation through materials, infiltration via leaks (both real and virtual), and outgassing from samples themselves. Any of these mechanisms can result in an increase in the concentration of absorbing species within the instrument and thus, a corresponding decrease in the optical throughput of the system. It follows that it may be advantageous to monitor the state of the environment so that appropriate steps may be taken to restore it as required; thereby ensuring that measurement accuracy is not compromised.

While many stand-alone methods, systems and sensors exist for monitoring the quality of an enclosed environment, the most direct and arguably most useful approach is to utilize the optical elements of the metrology instrument, in combination with a reference sample, to track optical throughput. The flowchart 100 in FIG. 1 illustrates how environmental monitoring may be achieved in this manner. First the volume of the instrument is evacuated to a pre-determined pressure $P_L$ using an appropriate vacuum system at step 110. Next, the instrument is backfilled with a non-absorbing gas to a pre-determined measurement pressure $P_H$ at step 120. Once the measurement pressure has been attained the intensity spectrum from the reference sample is immediately recorded at time $t_1$ as shown at step 130. The concentrations of absorbing species are presumed to be at their lowest achievable level at this point in time. Measurements on test samples are then performed at step 140 for some pre-determined time period, following which the intensity spectrum from the reference sample is again collected at time $t_2$ as shown at step 150. As shown at steps 160 and 170, the ratio of the two intensity spectra (time $t_1$ and time $t_2$) from the reference sample is then calculated and analyzed in order to determine the concentrations of absorbing species. At step 180, the determined concentrations are then compared to user-defined threshold values in order to determine whether or not the environment in the instrument is suitable to support further measurements. As indicated at step 190, if the environment is suitable, then measurements on test samples are again conducted for another pre-determined time period by returning control to step 140. Conversely, if the environment is no longer adequate (as indicated by step 195) then the environment is regenerated by re-initiating the evacuation/backfill procedure at step 110.

Figure 2:
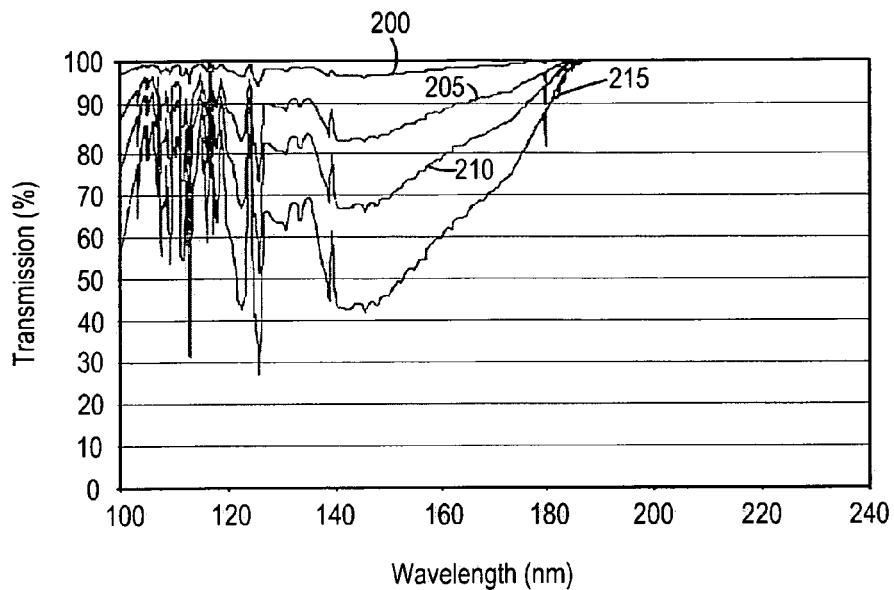
FIG. 2 illustrates exemplary environmental monitoring results using a broad-band VUV data set.

FIG. 2 presents ratios of reference measurements collected in the presence of an atmosphere of non-absorbing gas containing trace concentrations (1, 5, 10 and 20 PPM as indicated by plots 200, 205, 210, and 215 respectively) of both oxygen and water, to those collected in the presence of pure non-absorbing gas. As is evident from the figure the transmission through the controlled environment is considerably reduced at wavelengths below 190 nm as the concentrations of oxygen and water are increased. With a priori knowledge of the optical path length, instrumental pressure and absorption cross-section for oxygen and water, the concentrations of these species can be readily determined through analysis.

Figure 3:
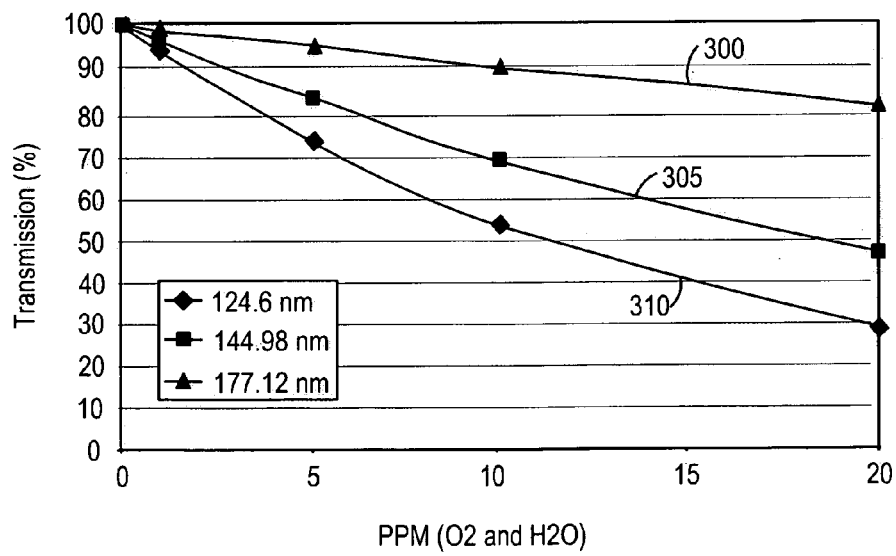
FIG. 3 illustrates exemplary environmental monitoring results using a select wavelength VUV data set.

Alternatively, the ratio of reference measurements at discrete wavelengths can also be used to provide a simple monitor of the quality of the controlled environment. In FIG. 3 the ratio of reference measurements performed in the presence of non-absorbing gas containing trace amounts of oxygen and water to those collected in the presence of pure non-absorbing gas are plotted as a function of oxygen and water concentration for VUV wavelengths 124.6 nm, 144.98 nm, and 177.12 nm (shown as plots 300, 305 and 310, respectively). In practice the measured transmission values can be compared to user-defined thresholds in order to determine the state of the controlled environment. The actual wavelengths used in the comparison can be chosen based on the absorption cross-section of the absorbing species of interest.

The environmental monitoring procedures described herein presume the spectral intensity of the VUV source does not change appreciably between the initial and final reference measurement times. While this may be a reasonable assumption in many instances, it is noted that the spectral intensity of the source could be independently monitored in order to account for intensity fluctuations in situations where significant variation was expected.

The time period over which such an instrument can be operated (and sample measurements can be reliably conducted) before requiring regeneration of the controlled environment could vary significantly depending on the design of the instrument and on the manner in which it is operated. For well-designed (i.e. leak-tight) systems operated so as to minimize exposure of internal surfaces (i.e. where samples are introduced via load-lock mechanisms) changes in the controlled environment will typically occur on a time scale considerably longer than that required to measure a given sample. Hence, it will often be possible to measure many such samples before requiring the controlled environment be regenerated. In any event, the reference measurement interval can be adjusted as required such that short intervals can be employed in cases where the environment is less stable and longer intervals can be used where the environment is more stable.

The controlled "measurement" environment established in the process outlined in the flowchart of FIG. 1 may be created by backfilling the instrument volume to a pre-determined pressure. Once this state is achieved the flow of purge gas to the instrument may be discontinued. An alternate method of operating such an instrument could be to equip the instrument with a purge valve set to a specific "relief" pressure so that purge gas could flow continuously through the instrument. In principle this could lessen or altogether eliminate the need to "regenerate" the measurement environment since the build-up of absorbing species like oxygen and water could be limited. Implementation of this approach is difficult in practice owing to the high flow rates required to maintain sufficiently low concentrations of absorbing species (owing to back-streaming of contaminants through purge exhaust). Furthermore, the continuous purge may induce pressure fluctuations that could adversely affect measurement stability.

A second difficulty associated with the use of VUV photons in optical metrology instrumentation relates to issues regarding surface contamination. Thin contaminate layers, which may only marginally affect the performance of optical surfaces at longer wavelengths, may significantly degrade the response of such elements at VUV wavelengths. In addition to adsorbed layers, which may be expected to readily form on optical surfaces under normal atmospheric conditions, organic and silicone-based films may also be unintentionally photo-deposited on such surfaces when irradiated with VUV photons in the presence of a contaminate-containing ambient.

Figure 4:
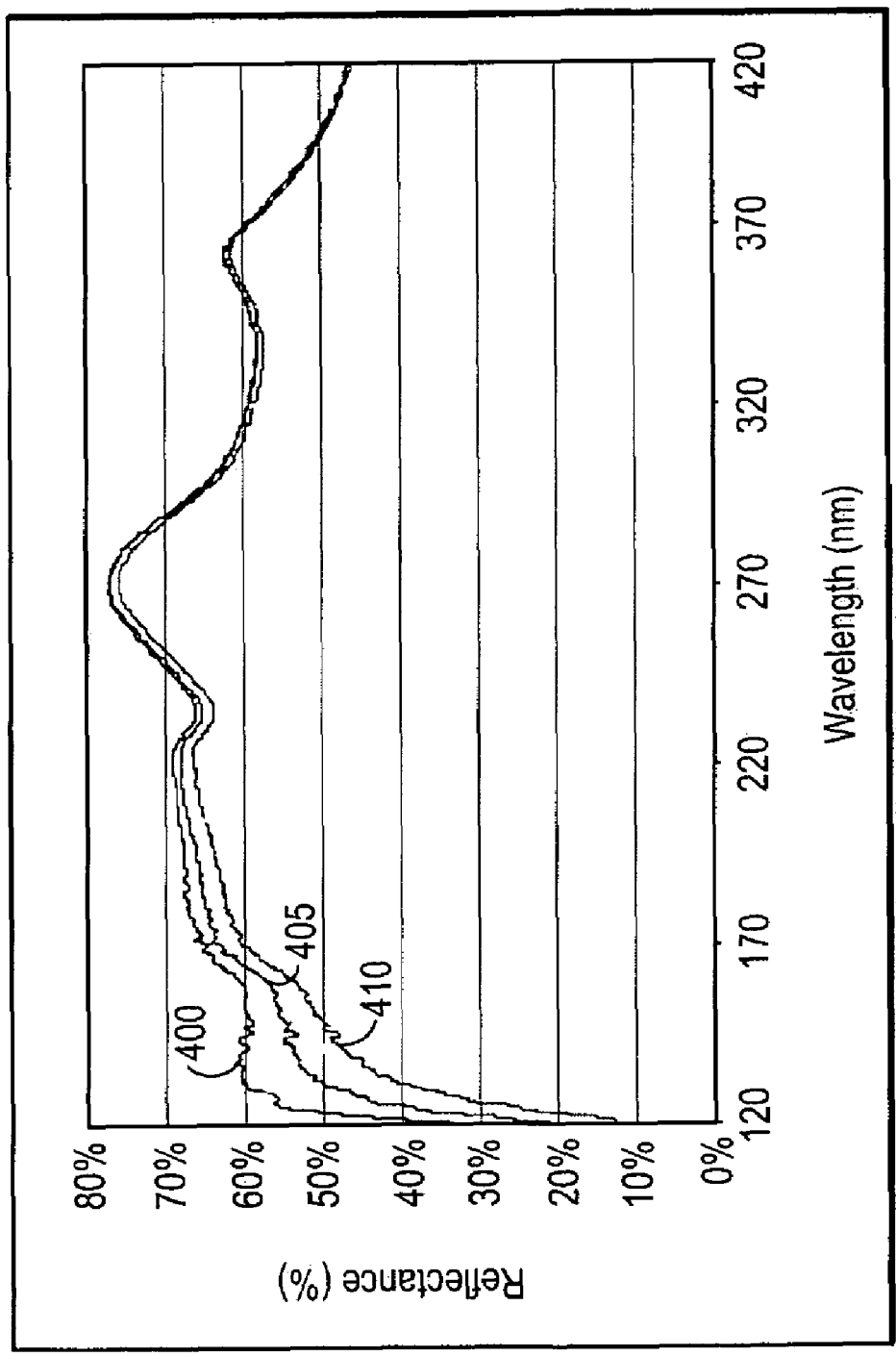
FIG. 4 illustrates exemplary reflectance data obtained from clean and contaminated silicon surfaces.

An example of the effect that contaminate layers may have on the VUV response of optical surfaces is provided in FIG. 4, wherein the reflectance of a "clean" silicon surface is compared to that of "slightly contaminated" and "more contaminated" surfaces as shown by plots 400, 405 and 410 respectively. As is evident from the figure the reflectance of the Si surface in the VUV region is significantly degraded as function of contaminate accumulation. As photons in optical metrology tools typically encounter many such surfaces as they travel from source to sample and finally to detector, it follows that even small reductions in the optical performance of each surface can seriously impact the overall optical throughput of the instrument.

Fortunately it is in many cases, possible to reduce, remove or altogether eliminate the build up of such contaminates on optical surfaces non-destructively through VUV irradiation in the presence of an ambient containing trace concentrations of oxygen. When exposed to VUV wavelengths diatomic oxygen is dissociated into atomic oxygen, which then reacts with diatomic oxygen to form ozone. Both atomic oxygen and ozone are highly reactive and capable of oxidizing surface contaminants forming gaseous products, which may then be liberated.

Figure 5A:
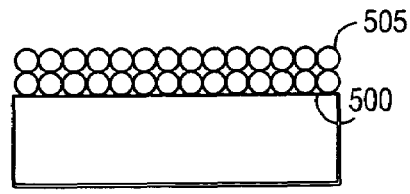
FIG. 5(a) illustrates an optical surface with contaminate layer.
Figure 5B:
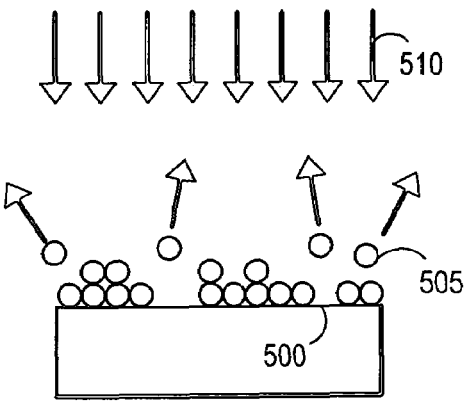
FIG. 5(b) illustrates VUV exposure in an oxygen-containing ambient resulting in cleaning.
Figure 5C:
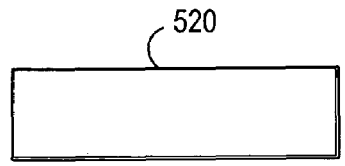
FIG. 5(c) illustrates a clean optical surface following treatment.

This photo-etch cleaning process is illustrated schematically in FIG. 5. In FIG. 5A a contaminated optical surface 500 is shown having contaminates 505. In FIG. 5B the contaminated optical surface 500 is exposed to VUV radiation 510 in the presence of an oxygen-containing ambient resulting in the removal of contaminates 505 from the surface through the reactions outlined above. In FIG. 5C the resultant "clean" optical surface 520 is presented.

With certain contaminants (for example halogenated organic compounds and organosilicones) the photo deposition reactions may be irreversible and hence, it may not be possible to fully remove them through photo-etch processes. In such instances irradiation of surfaces with VUV photons in the presence of an ambient consisting largely of oxygen, but with even trace levels of contaminate compounds, may only result in continued growth of the contaminate layer.

Figure 6:
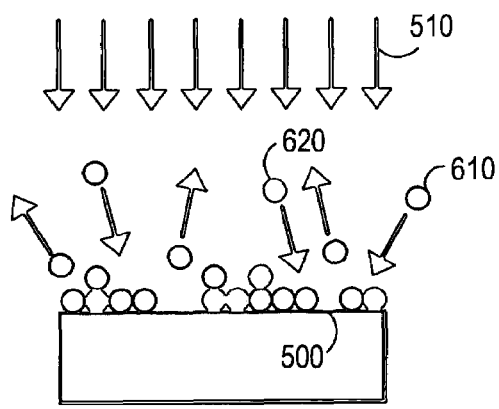
FIG. 6 illustrates reversible deposition and etch of one contaminant specie and irreversible deposition of a second contaminant specie resulting from VUV irradiation in the presence of an ambient containing both contaminants and oxygen.

In a more general case a surface may be exposed to VUV radiation in the presence of an ambient containing oxygen, contaminates conducive to both photo-deposit and photo-etch (i.e. those formed via reversible reactions) and contaminates which photo-deposit, but can not be photo-etched (i.e. those formed via irreversible reactions). In such circumstances there could be at least three distinct processes taking place; reversible deposition processes, irreversible deposition processes and back-reaction processes via etching. These three processes are depicted graphically in FIG. 6 by the hollow circles 610 and filled circles 620 moving towards the surface (reversible and irreversible deposition respectively) and by the hollow circles 610 moving away from the surface (etching), respectively. The relative rates associated with these processes will depend on a variety of factors including the surface concentration of adsorbed contaminants, the oxygen concentration, the absorption cross section of said contaminants and the associated VUV photon flux.

As oxygen may play a crucial role in the photo-etch process it follows that it may be beneficial to monitor and control the concentration of oxygen contained within the instrumental volume. In this manner, trace levels of oxygen (or clean dry air) could be intentionally added to the non-absorbing gas of the backfill so as to promote the cleaning processes without significantly compromising VUV photon flux for measurement purposes. Depending on the relative rates of contamination and etch it may be possible to operate VUV optical instrumentation in such a manner as to not facilitate the build-up of undesirable materials to begin with (i.e. where etch rates exceed contamination rates). In cases where significant quantities of contaminants are already present on optical surfaces, the cleaning time required to remove such films may be greatly reduced by temporarily increasing the concentration of oxygen above the levels normally employed for data acquisition.

The concentration of trace quantities of oxygen intentionally added to the controlled environment of the instrument could be monitored just as the unintentional accumulation of oxygen and moisture (due to leaks, etc.) was tracked using the environmental monitoring methodology of FIG. 1. Trace quantities of gases like oxygen could be accurately added to the volume of the instrument using a mass flow controller. Practical implementation could be achieved by modifying the methodology of FIG. 1 such that a fixed quantity of oxygen was added to the volume of the instrument immediately prior to the commencement of sample testing. To verify that the appropriate quantity of oxygen was added to the system, the intensity spectrum from the reference sample could be recorded and compared to that obtained immediately following backfill with the non-absorbing gas. Thus, for example, trace quantities of oxygen for example in the range of 1 ppm or less and more preferably in the range of 0.1 ppm or less can be added to an controlled environment in order accelerate various cleaning mechanisms. In one embodiment the controlled environment may be at a sub-atmospheric pressure.

In principal, all optical surfaces in VUV metrology instruments are susceptible to contamination effects. This includes not only optical elements (i.e. windows, beam splitters, mirrors, etc), but also the surfaces of samples themselves. As the concentration of contaminants in metrology instruments may be expected to vary considerably with changes in the tool ambient, and through the introduction of samples, it follows that in order to achieve optimum system performance it may be beneficial to monitor the accumulation (or removal) of said contaminants over time so that appropriate cleaning measures may be taken.

If such surfaces are to be effectively cleaned via photo-etching processes it follows that the VUV relative flux profile received by optical surfaces during cleaning should closely match that received during the initial photo-deposition process. Consequently, to achieve optimum cleaning results it may be desirable to precisely configure and align VUV cleaning systems with VUV optical metrology instruments in such a manner as to ensure the VUV flux profiles received by optical surfaces are closely matched.

Accordingly it may be advantageous if VUV cleaning capabilities could be integrated in to optical metrology instrumentation in such a manner as to not require their precise configuration and alignment. Furthermore, if such capabilities could be incorporated in a means that required very few additional components, above and beyond those already present in the optical metrology tool, system design and cost requirement could be greatly reduced. An innovative means of accomplishing this is to utilize the optical elements of the metrology instrument itself, in combination with a reference sample, to track the contamination state of the system.

Figure 7:
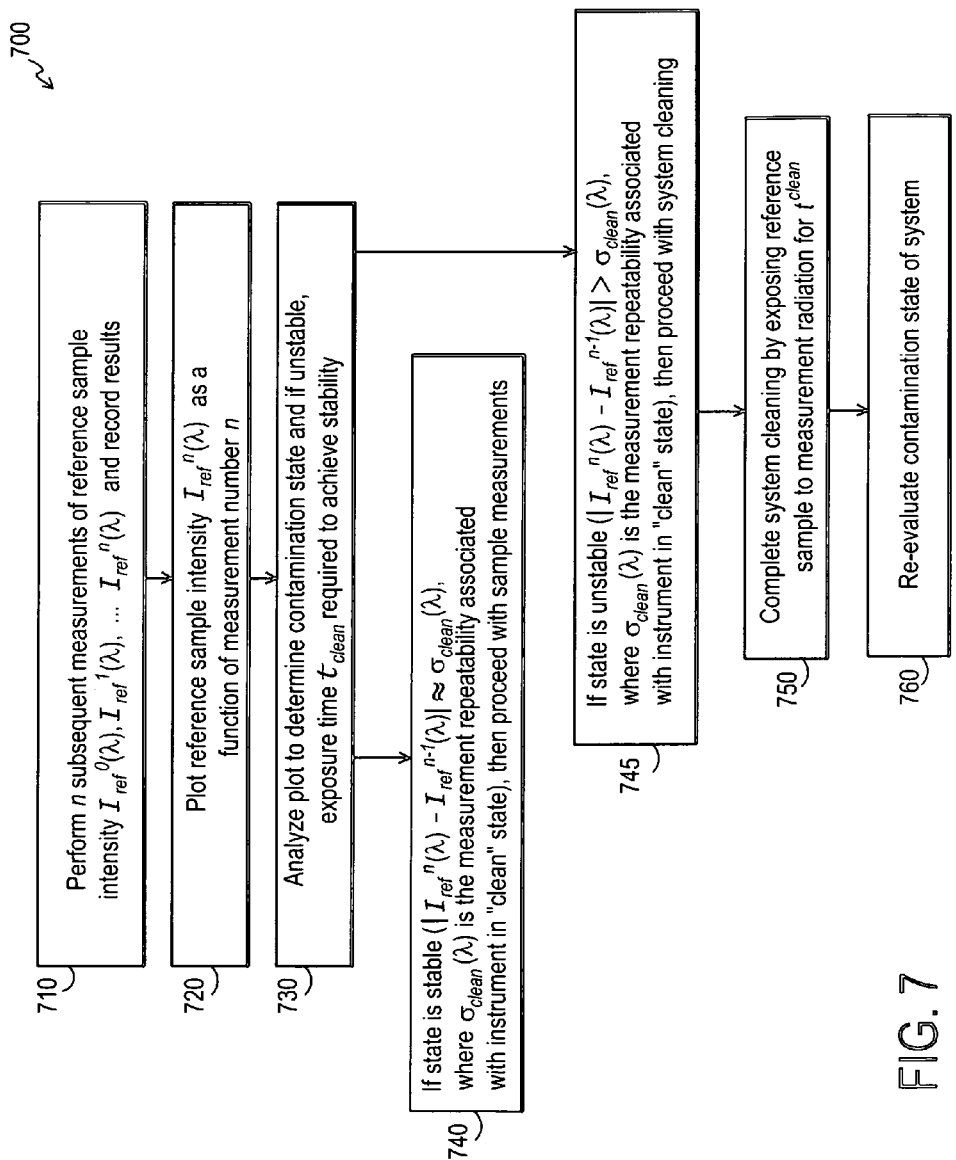
FIG. 7 is an exemplary system contaminant monitoring flowchart.

The flowchart 700 in FIG. 7 illustrates how contaminant monitoring may be achieved in this manner. First a series of n monitoring measurements of the reference sample intensity are performed on the reference sample and recorded as shown in step 710. Each measurement exposes the optical path of the instrument (and each of the optical elements encountered en route) to a certain flux of VUV radiation for a known time interval. Hence, each measurement may be considered to impart a specific dose of VUV radiation upon the optical surfaces in the instrument. Next, the reference sample intensity may be analyzed as a function of the measurement number n. For example, the reference sample intensity may be plotted as a function of the measurement number n as shown in step 720. Thus, by recording the intensity at the detector as a function of the number of measurements it is possible to effectively track the optical throughput of the system as a function of VUV exposure dose. In one embodiment, the number of measurements may be ten or less. If the environment of the system is sufficiently controlled, the number of measurements may only be two.

Following these reference measurements the recorded results can be analyzed to determine whether or not the cleaning process is complete and hence the optical throughput of the tool stable. For example, as shown in step 730, the plot of the reference sample intensity as a function of measurement number n may be analyzed to determine the contamination state, and if unstable, the exposure time $t_{clean}$ required to achieve stability. If the system is found to be in a stable state then sample measurements can be performed. For example as shown in step 740 the state may be considered stable if the difference between the reference sample intensity for two successive measurements (n and n−1) is within a range that is within a desired measurement repeatability that is associated with a "clean" state. However, as shown in step 745, the state may be considered unstable if the difference between the reference sample intensity for two successive measurements (n and n−1) is greater than the range that is within a desired measurement repeatability that is associated with a "clean" state. If the system is found unstable (indicating the cleaning process is incomplete) then the exposure dose required to achieve system stability can be estimated. This exposure dose can be converted to an effective measurement time to which the system (and reference sample) can be exposed as indicated in step 750. The exposure may in one embodiment be made in a single event, as opposed to exposure through a series of individual reference measurements. Following exposure of the system to the requisite cleaning dose, the series of monitoring measurements on the reference sample can again be performed as indicated by the re-evaluation step 760. The process may be repeated until it is confirmed that the instrument is in fact in a stable "clean" state. As shown in the exemplary technique of FIG. 7, a change between two intensity measurements was determined by subtracting one intensity measurement from another. However, it will be recognized that a difference or change in two intensity measurements may be identified by a wide range of methods of comparing the two measurements and therefore the variation between two measurements may be quantified in a wide range of manners. For example, ratios may also be utilized to quantify the variation. Thus, it will be recognized that the measurement data may be analyzed, compared and quantified with a wide range of mathematical methods while still utilizing the concepts described herein. In addition, although described with relation to evaluating two successive measurements (n and n−1), it will be recognized that the two measurements need not be successive but rather merely any two measurements may be evaluated to determine a variation from one measurement to the another.

It follows that by tracking the stability of the system (as a function of time, usage, etc.) the details (i.e. reference measurement frequency, effective dose per exposure, trace concentration of oxygen present in instrumental volume, etc) associated with the cleaning process can be adjusted so as to ensure efficient instrument cleaning and hence enhanced system stability. In this manner the tool can be operated in such a fashion as to optimize instrument performance.

Figure 8:
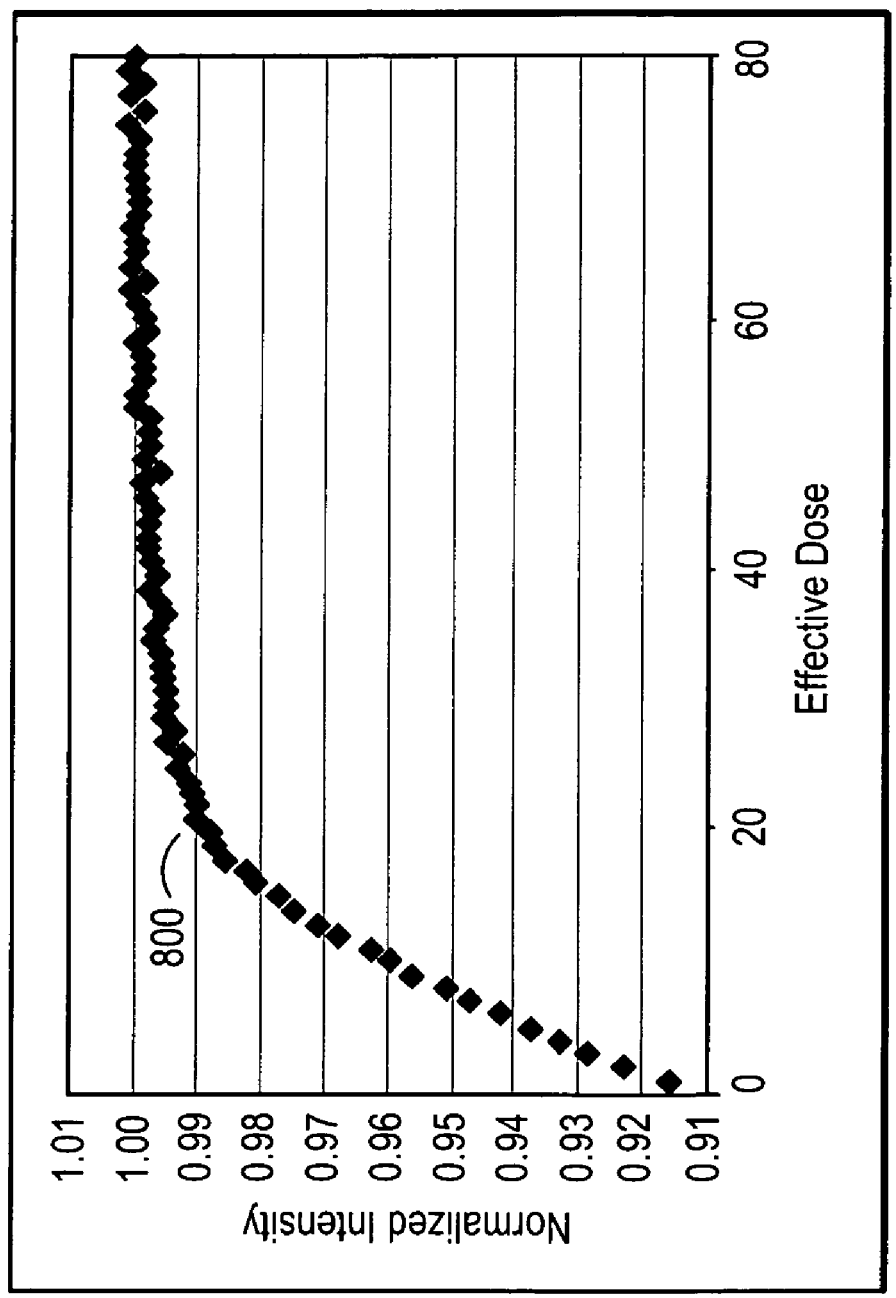
FIG. 8 illustrates exemplary contaminate monitoring data using a select VUV wavelength.

An example of the potential results from this process are presented as plot 800 in FIG. 8, wherein the normalized intensity from a reference sample at a single VUV wavelength is plotted as a function of effective dose. As is evident from the figure the intensity from the reference sample increases generally linearly upon exposure for a period of time before stabilizing. It follows that the ability of an optical instrument to perform accurate measurements, prior to completion of such a cleaning process, would be significantly compromised if such cleaning was not performed.

Non-optical surfaces within such instruments must also be considered as they can serve as sources of contaminants that may be adsorbed on them, and which may be liberated at a later time. Accordingly, it is desirable to manufacture such surfaces in a manner so as to minimize sticking probabilities for potential contaminants. This may involve specific machining processes and/or the application of appropriate coatings to ensure vacuum compatibility is achieved.

In order to lessen the migration of contaminants from extraneous surfaces within the instrument to optical elements it is advantageous to operate the tool in such a manner as to minimize the evaporation rate of such species. At a given temperature, the evaporation rate of molecules will increase as the ambient pressure is reduced. Additionally, the mean free path of these molecules will also increase under such conditions. As a consequence such molecules will exhibit a greater propensity to distribute themselves throughout the available volume, increasing the likelihood of their encountering optical surfaces and sticking to them. Thus, from a contamination perspective it is desirable to minimize the time wherein the volume of VUV optical instrumentation is maintained at reduced pressures.

Just as optical elements in VUV metrology tools are susceptible to contamination effects, so are samples to be measured themselves. The extent of sample contamination will depend largely on both the environment to which samples are exposed to, following their creation, and on the duration of that exposure. Hence, to help achieve accurate measurements of sample properties it is desirable to properly account for surface contaminant layer(s) which may exist. This is particularly important in cases where the samples under study are comprised of ultra-thin films whose thicknesses are comparable to those of the contaminant layers themselves. This importance is further underscored in situations where the contaminant layer(s) exhibit a high degree of absorbance, relative to the ultra-thin films under study.

The conventional approach to this problem has been to attempt to completely remove the contaminate layer from the entire surface of the sample prior to initiating measurements. Typically, whole wafer cleaning is performed using thermal heating, microwave radiation, UV radiation or some combination of these or other techniques. There are numerous difficulties associated with such full wafer cleaning methodologies. Such systems are often relatively large and as such likely to be configured as stand-alone systems, outside the controlled environment of a VUV optical metrology instrument. As a result, samples must be transferred between the cleaning system and the metrology instrument, giving rise to the possibility of re-contamination.

Furthermore, while moisture may be readily removed using whole wafer cleaning methodologies, complete and uniform removal of other contaminants may prove problematic. This follows from the difficulties associated with generating a power flux possessing sufficient energy, amplitude and spatial uniformity to ensure that contaminants are fully removed from all regions of the sample. Residual contaminants following cleaning may lead to inaccurate measurement results and misleading conclusions regarding the spatial uniformity of sample properties.

Stand-alone spot-cleaning techniques suffer from shortcomings even in cases where they are integrated into the controlled environment of a VUV metrology instrument. To ensure accurate measurements results are obtained it is may be desirable to precisely align spot-cleaning systems with optical metrology instrumentation such that cleaning and measurement spot locations are coincident.

Accordingly it would be advantageous if spot-cleaning capabilities could be integrated in to optical metrology tools in such a manner as to avoid alignment concerns through use of a common optics module. Furthermore, if such capabilities could be incorporated in a means that required very few additional components, above and beyond those already present in the optical metrology tool, system design and cost requirement could be greatly reduced.

A novel means of accomplishing this is to utilize the measurement radiation itself to both clean and characterize the sample. Hence, discrete locations on samples can be cleaned via exposure to measurement radiation immediately preceding measurement. In addition to eliminating cleaning/measurement alignment concerns entirely, this approach avoids needlessly "treating" the vast bulk of the sample surface area. The techniques provided herein may still be utilized however through the use of separate light sources utilized as a cleaning light source and a measurement light source. One, both or neither of such light sources may be a VUV light source.

A further benefit of this technique is that it offers the ability to readily measure and characterize the contaminant layer itself. The manner in which this can be accomplished is illustrated in the flowchart 900 of FIG. 9. By obtaining an optical response from a contaminated sample before and after removal of the contamination layer and then analyzing the results it is possible to determine the properties (thickness, optical properties, composition, roughness, etc.) of the contaminant layer. With this knowledge in hand, data can then be collected from other contaminated locations on the sample and analyzed in order to characterize the properties of the sample. In other words, once the properties of the contaminant layer on a given sample are determined it is in principle, possible to accurately characterize other locations on the sample without first cleaning them. In addition to the obvious throughput advantages, owing to the decrease in combined clean/measurement cycle time, this technique can also provide valuable information regarding the contaminant layer itself which may be used to refine sample processing methodologies.

Figure 9:
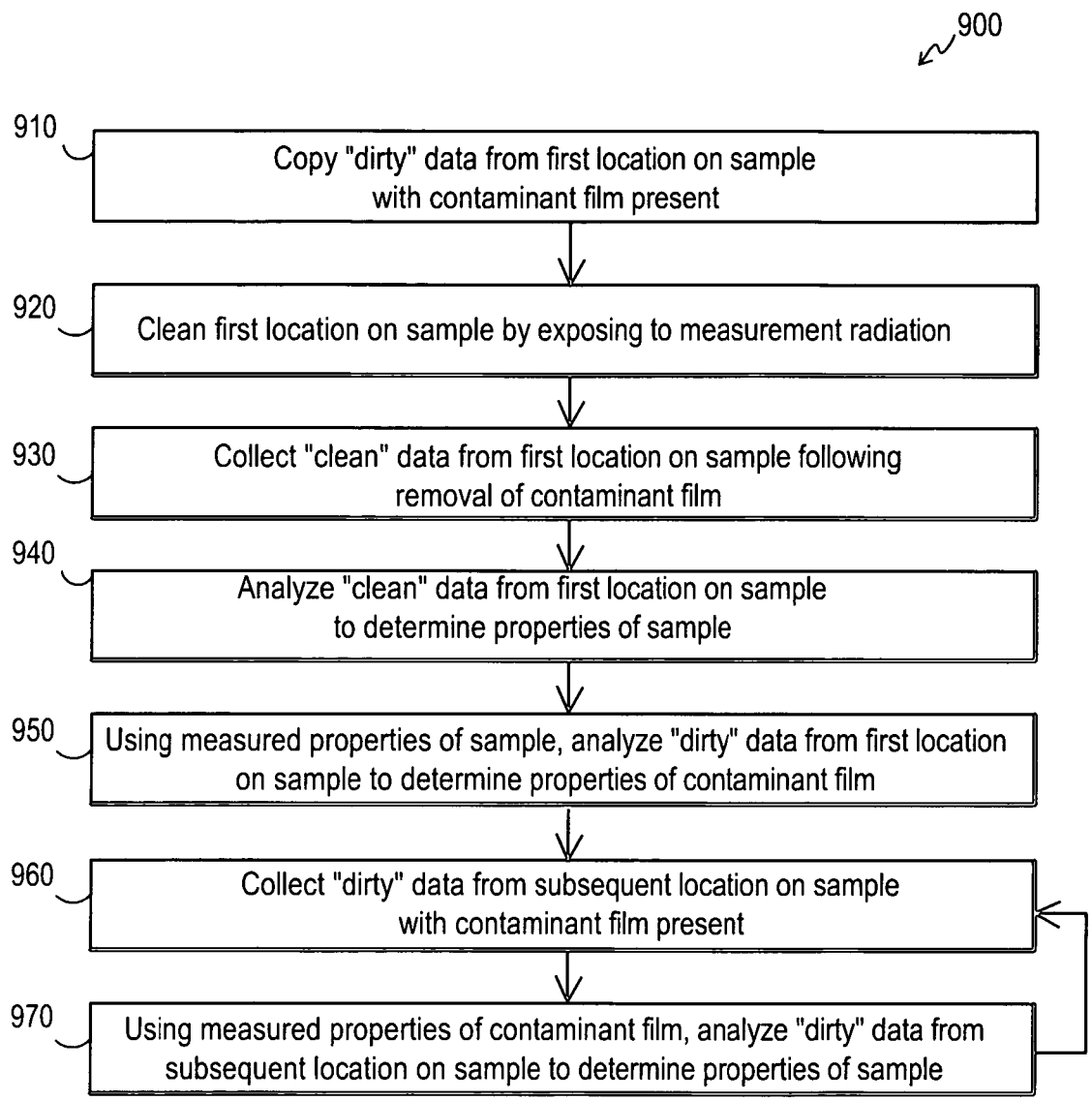
FIG. 9 is an exemplary contaminated sample measurement flowchart.

As shown in FIG. 9 step 910, reflectance data may first be collected from a first location of a "dirty" sample which has a contaminant film present. Next at step 920 the first location on the sample is cleaned by exposing the location to measurement radiation. At step 930 "clean" data may then be collected from the first location following the removal of contaminate film in step 920. At step 940 the clean data from the first location of the sample may be analyzed to determine the properties of the sample. At step 950 the measured properties of the sample from step 940 may be utilized to analyze the dirty data from the first location (the data from step 910) in order to determine properties of the contaminant film. Next at step 960 "dirty" data may be collected from another location on the sample with the contaminant film present. Then in step 970 by using the "dirty" data from the other location obtained in step 960 and the measured properties of the contaminant film obtained in step 950, properties of the sample may be determined in step 970 for the other location without requiring a cleaning step of the other location. Multiple locations may be analyzed in this manner by returning control from step 970 to 960 and repeating the process.

It follows that the method of FIG. 9 could be employed in a manner whereby the properties of the contaminant layer are determined at one or some number of locations on a given sample, or series of samples, and then used during the analysis of subsequent measurement locations on the same or different samples, once the validity of the approach has been demonstrated. Thus, the contaminant layer need not be analyzed at all the measurement locations. Alternatively, in situations where the nature of the contaminant layer is expected to vary significantly from one location to the next, it is possible to clean every measurement location prior to data collection. Additionally, it is also possible to measure each location on the sample prior to and immediately following cleaning in order to determine the properties of both the contaminant layer and the underlying sample.

Of course, it is possible to combine the use of this integrated spot-cleaning methodology with other stand-alone, whole wafer or spot-cleaning techniques. Such an approach may be advantageous in situations where samples are highly contaminated and/or where many locations on a given sample are to be measured. Under such circumstances the combination of cleaning methods may aid to speed the cleaning process.

The same sample cleaning methodology outlined herein can also be used to prepare calibration and/or reference samples utilized by optical metrology systems to ensure that a high level of measurement accuracy is achieved. Furthermore, the properties of these "cleaned" samples can be monitored over time to track the "health" of such samples. In this manner the repair and/or replacement of such samples could be scheduled to coincide with other preventative maintenance activities.

In some instances further insight into the characteristics of contaminate layers themselves may be gained through observation of the response of such layers to the cleaning process. That is, by recording the removal rate of the contaminate film as a function of accumulated dose it may be possible to determine something of its chemical nature. Once correlated with additional analytical data, a library of cleaning response profiles could be generated. This library could then be referred to during subsequent measurements wherein unknown contaminants were to be characterized.

Figure 10:
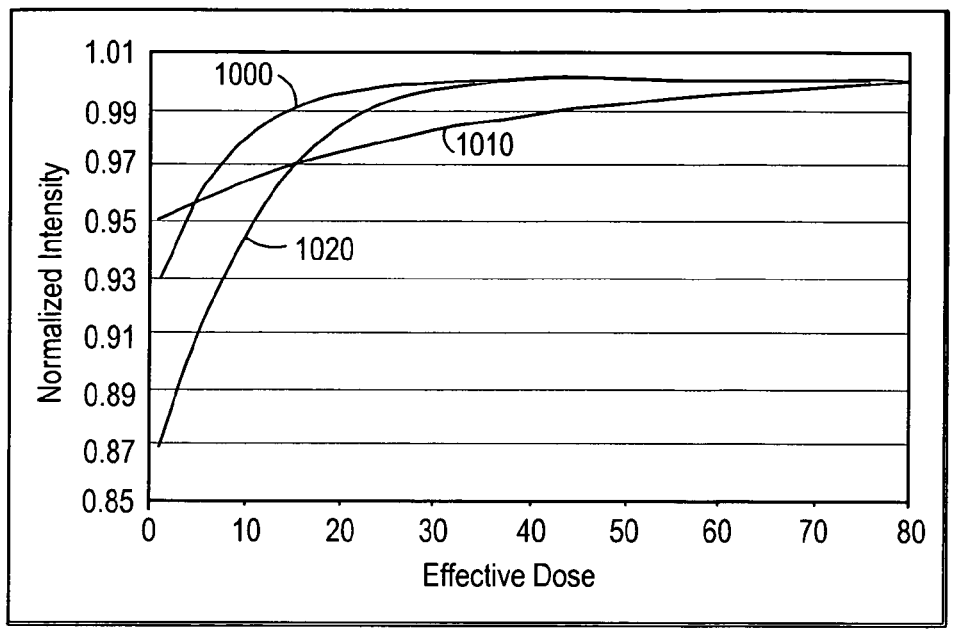
FIG. 10 illustrates an exemplary cleaning response profile for three different contaminate films.

As an example, FIG. 10 presents exemplary cleaning response profiles for three different contaminate layers 1000, 1010, and 1020. The exemplary cleaning response profiles illustrate the profile variations that may be seen from different contaminate layers. With these profiles stored in a cleaning response library, profiles from unknown contaminant films could be categorized through comparison. The profiles could be compared directly or could be fit using a parameterized model, wherein the resultant parameter values could be used to distinguish between contaminant species.

Thus as described above, a property of a sample layer may be changed by exposure of the sample to optical radiation and the changes may be characterized through the use of measurements performed before and after the exposure to optical radiation. In the example described above the change may comprise removing a contaminant layer from the sample. However, it will be recognized that other changes in the sample may be characterized. Thus, for example, a contaminant layer need not be present but rather the some other layer or portion of the sample may be characterized. In one embodiment, a property of a layer or portion of the sample that is to be analyzed through use of the optical metrology tool may be characterized. In such an embodiment, the layer or portion may remain after the exposure to optical radiation however some state of the layer or portion may be changed. By characterizing the changes that occur, information about the original properties of the layer or portion may be obtained.

For example, exposure to the optical radiation may change the bond structure, species concentrations, or other physical properties of the sample. In such examples, the original bond structures, species concentrations/migration or other physical properties may be quantifiable based upon the amount of change detected with some dose of optical radiation. Thus, how the layer reacts to the optical radiation may render useful information about the original properties of the layer. The changes in the layer may be analyzed through quantified measurements of the change detected, alternatively through comparison to known optical response profiles (such as stored in a response profile library) or other techniques.

In one example, a silicon oxide film that contains nitrogen may be characterized through such techniques. For example, VUV optical exposure may preferentially impact nitrogen contained in such film by causing nitrogen migration and/or changing the bond structure holding the nitrogen in such films. Detected optical response variations before and after the optical radiation exposure may thus provide useful information with regard to the original status of the nitrogen bonds (tightly bonded, loosely bonded, etc.), the nitrogen concentration, or the like. It will thus be recognized that in a general form the techniques provided herein provide for detection of characteristics of a sample through the analysis of a film before and after a property of the film has been changed due to exposure to optical radiation.

In order to help achieve accurate and repeatable results from optical metrology instruments operating in the VUV, the environmental monitoring methodology of FIG. 1, the contaminant monitoring methodology of FIG. 7 and the sample cleaning methodology of FIG. 9 may be combined to form the underlying operation basis for such equipment.

Example of a VUV optical metrology instrument well suited to benefit from use of the methods herein described are disclosed in U.S. application Ser. No. 10/668,642, filed on Sep. 23, 2003, now U.S. Pat. No. 7,067,818 and U.S. application Ser. No. 10/909,126, filed on Jul. 30, 2004, now U.S. Pat. No. 7,126,131 the disclosures of which are both expressly incorporated herein by reference. The metrology instrument may be a broad-band reflectometer specifically designed to operate over a broad range of wavelengths, including the VUV.

Figure 11:
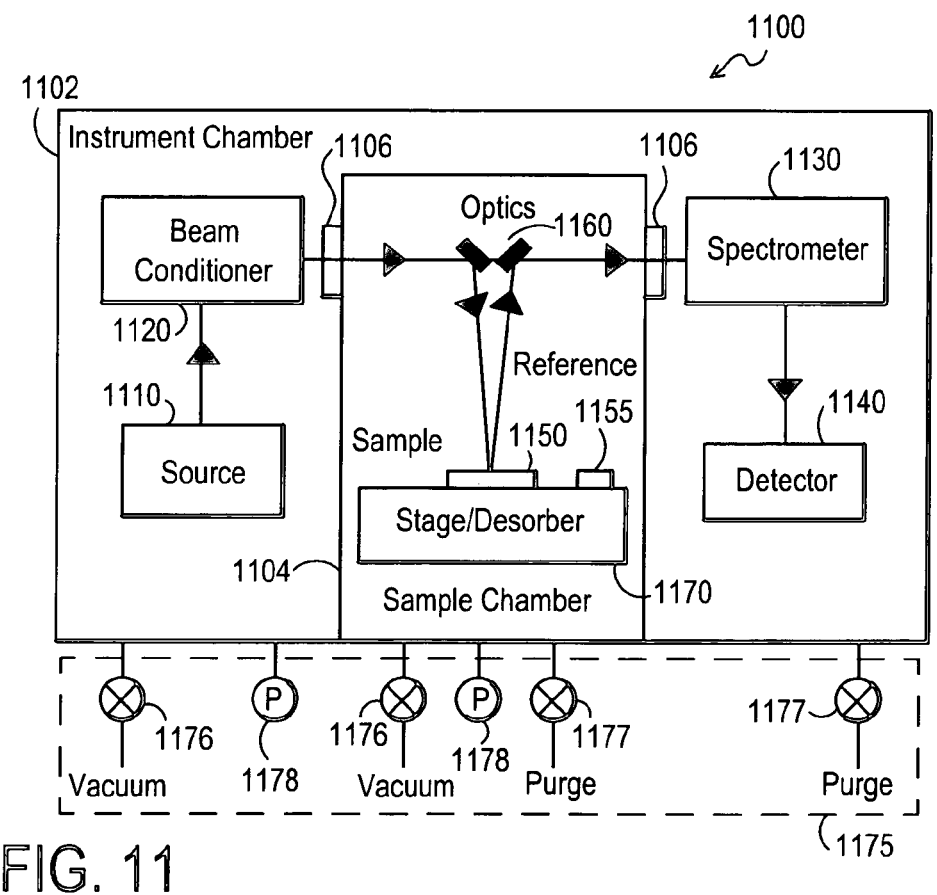
FIG. 11 illustrates an exemplary schematic representation of a VUV reflectometer.

An example of such an instrument 1100 is presented in FIG. 11. As is evident the source 1110, beam conditioning module 1120, optics (not shown), spectrometer 1130 and detector 1140 are contained within an environmentally controlled instrument (or optics) chamber 1102. The sample 1150, additional optics 1160, motorized stage/sample chuck 1170 (with optional integrated desorber capabilities) and reference sample 1155 are housed in a separate environmentally controlled sample chamber 1104 so as to enable loading and unloading of samples without contaminating the quality of the instrument chamber environment. The instrument and sample chambers are connected via a controllable coupling mechanism 1106 which permits the transfer of photons, and if so desired the exchange of gases to occur. Both the instrument chamber 1102 and sample chamber 1104 are connected to vacuum and purge sub-system 1175 that is complete with appropriate vacuum connections 1176, valves, purge connections 1177 and pressure gauges 1178 such that environmental control can be independently exercised in each chamber. In this manner, the environmental vacuum and backfill techniques described above may be accomplished upon each chamber independently or together. Thus, the vacuum and backfill techniques (one or both) may be performed upon the instrumentation/optics chamber, the sample chamber and/or both chambers.

Additionally a processor (not shown) located outside the controlled environments may be used to coordinate and facilitate the automated monitoring methodologies and to analyze the measured data. It is recognized that the processor may be any of a wide variety of computing means that may provide suitable data processing and/or storage of the data collected.

While not explicitly shown in FIG. 11 it is noted that the system could be equipped with a robot and other associated mechanized components to aid in the loading and unloading of samples in an automated fashion, thereby further increasing measurement throughput. Further, as is known in the art load lock chambers may also be utilized in conjunction with the sample chamber to improve environmental control and increase the system throughput for interchanging samples.

In operation light from the source 1110 is modified, by way of the beam conditioning module 1120 and directed via delivery optics through the coupling mechanism 1106 and into the sample chamber 1104, where it is focused onto the sample 1150 by focusing optics 1160. Light reflected from the sample 1150 is collected by the focusing optics 1160 and re-directed out through the coupling mechanism 1106 where it is dispersed by the spectrometer 1130 and recorded by the detector 1140. The entire optical path of the device is maintained within controlled environments which function to remove absorbing species and permit transmission of VUV photons.

Figure 12:
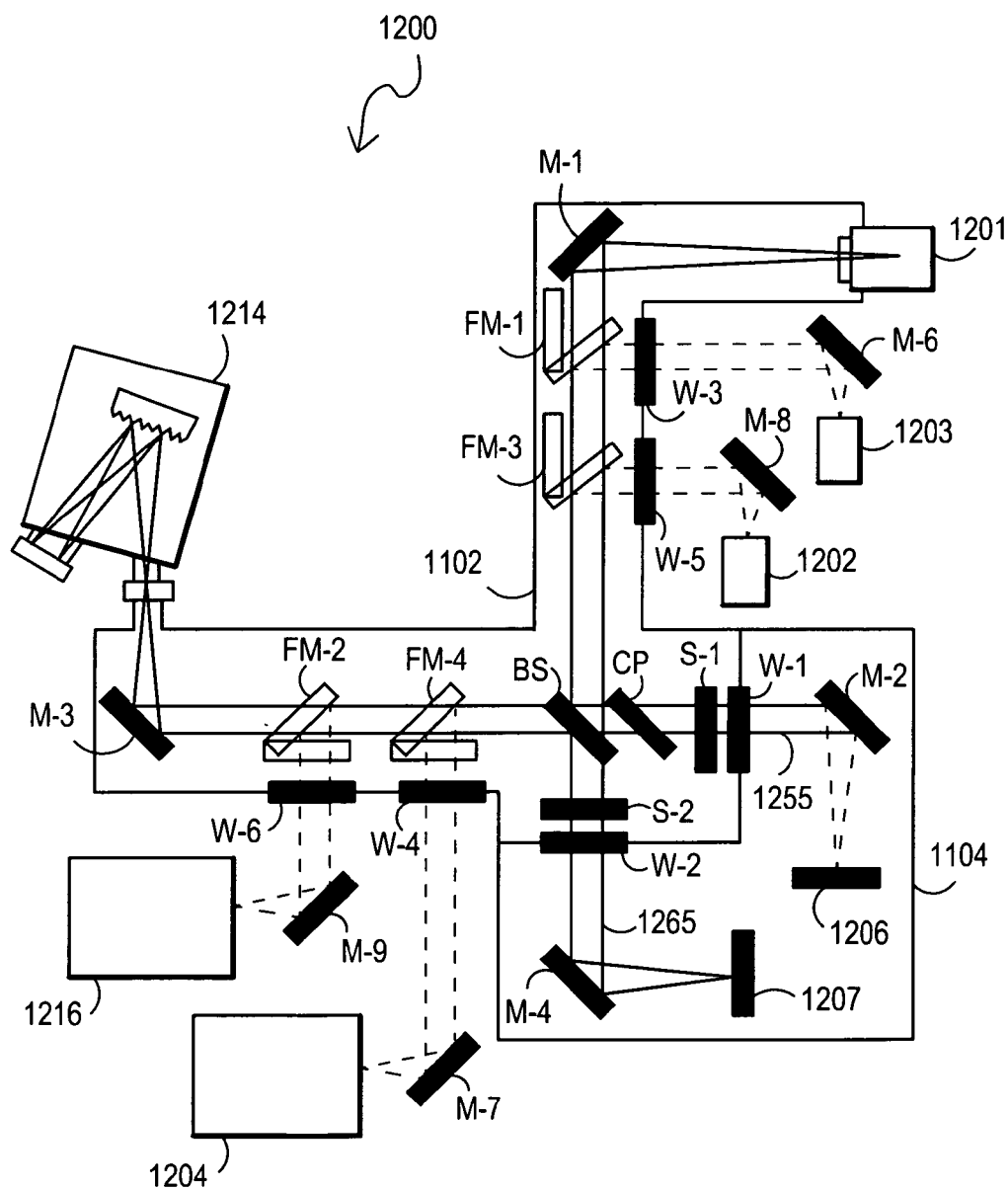
FIG. 12 illustrates a broad-band referencing reflectometer covering three spectral regions including the VUV.

A more detailed schematic of the optical aspects of the instrument is presented in FIG. 12. The instrument is configured to collect referenced broad band reflectance data in the VUV and two additional spectral regions. In operation light from these three spectral regions may be obtained in either a parallel or serial manner. When operated in a serial fashion reflectance data from the VUV is first obtained and referenced, following which, reflectance data from the second and then third regions is collected and referenced. Once all three data sets are recorded they are spliced together to form a single broad band spectrum. In parallel operation reflectance data from all three regions are collected, referenced and recorded simultaneously prior to data splicing.

The instrument is separated into two environmentally controlled chambers, the instrument chamber 1102 and the sample chamber 1104. The instrument chamber 1102 houses most of the system optics and is not exposed to the atmosphere on a regular basis. The sample chamber 1104 houses the sample and sample and reference optics, and is opened regularly to facilitate changing samples. For example, the instrument chamber 1102 may include mirrors M-1, M-2, M-3, and M-4. Flip-in mirrors FM-1 and FM-3 may be utilized to selective chose which light source 1201, 1202 and 1203 is utilized (each having a different spectral region). Flip-in mirrors FM-2 and FM-4 may be utilized to selective chose one of spectrometers 1204, 1216, and 1214 (again depending upon the chosen spectral region). Mirrors M-6, M-7, M-8 and M-9 may be utilized to help direct the light beams as shown. Windows W-1 and W-2 couple light between the instrument chamber 1102 and sample chamber 1104. Windows W-3, W-4, W-5 and W-6 couple light into and out of the instrument chamber 1102. Beam splitter BS and shutters S-1 and S-2 are utilized to selectively direct light to a sample 1206 or a reference 1207 with the assistance of mirrors M-2 and M-4 as shown (the reference may be a mirror in one embodiment). The sample beam passes through compensator plate CP. The compensator plate CP is included to eliminate the phase difference that would occur between the sample and reference paths resulting from the fact that light traveling in the sample channel passes through the beam splitter substrate but once, while light traveling in the reference channel passes through the beam splitter substrate three times due to the nature of operation of a beam splitter. Hence, the compensator plate may be constructed of the same material and is of the same thickness as the beam splitter. This ensures that light traveling through the sample channel also passes through the same total thickness of beam splitter substrate material.

When operated in a serial fashion VUV data is first obtained by switching the second spectral region flip-in source mirror FM-1 and third spectral region flip-in source mirror FM-2 into the "out" position so as to allow light from the VUV source to be collected, collimated and redirected towards beam splitter element BS by the focusing mirror M-1. Light striking the beam splitter is divided into two components, the sample beam 1255 and the reference beam 1265, using a near-balanced Michelson interferometer arrangement. The sample beam is reflected from the beam splitter BS and travels through the compensator plate CP, sample shutter S-1 and sample window W-1 into the sample chamber 1104, where it is redirected and focused onto the sample 1206 via a focusing mirror M-2. The reference shutter S-2 is closed during this time. The sample window W-1 is constructed of a material that is sufficiently transparent to VUV wavelengths so as to maintain high optical throughput.

Light reflected from the sample is collected, collimated and redirected by the sample mirror M-2 back through the sample window, where it passes through the sample shutter and compensator plate. The light then continues on unhampered by the first spectral region flip-in detector mirror FM-2 and the second spectral region flip-in detector mirror FM-4 (switched to the "out" position), where it is redirected and focused onto the entrance slit of the VUV spectrometer 1214 by the focusing mirror M-3. At this point light from the sample beam is dispersed by the VUV spectrometer and recorded by its associated detector.

Following collection of the sample beam, the reference beam is measured. This is accomplished by closing the sample shutter S-1 and opening the reference shutter S-2. This enables the reference beam to travel through the beam splitter BS, reference shutter S-2 and reference window W-2 into the sample chamber 1104, wherein it is redirected and focused by mirror M-4 onto the plane reference mirror 1207 which serves as the reference. The reference window is also constructed of a material that is sufficiently transparent to VUV wavelengths so as to maintain high optical throughput.

Light reflected from the surface of the plane reference mirror 1207 travels back towards the focusing reference mirror M-4 where it is collected, collimated and redirected through the reference window W-2 and the reference shutter S-2 towards the beam splitter BS. Light is then reflected by the beam splitter towards the focusing mirror M-3 where it is redirected and focused onto the entrance slit of the VUV spectrometer 1214.

The path length of the reference beam 1265 is specifically designed to match that of the sample beam 1255 in each of the environmentally controlled chambers. It follows that the quality of the controlled environments of the instrument can be assessed by monitoring the intensity from the reference arm as described earlier in FIG. 1. As described above with reference to FIG. 7, the amount of optical radiation that various optical elements of the system are exposed to may impact the amount of surface contaminates that may be present upon the various optical elements. Thus, to help further balance the reference path that the reference beam follows and the sample path that the sample path follows it may be desirable to balance the optical radiation dose that each path is exposed to. In this manner, in addition to the balancing of the optical path lengths and elements, the contaminates related to the optical elements may also be relatively balanced between each path. In addition, the techniques for determining the contamination state of the optical path described herein may be separately performed upon each path to monitor the state of each of the paths.

Following measurement of the VUV data set, the second spectral region data set is obtained in a similar manner. During collection of the second region spectral data both the second spectral region source flip-in mirror FM-1 and the second spectral region detector flip-in mirror FM-2 are switched to the "in" position. As a result, light from the VUV source 1201 is blocked and light from the second spectral region source 1203 is allowed to pass through window W-3, after it is collected, collimated and redirected by its focusing mirror M-6. Similarly, switching the second spectral region detector flip-in mirror FM-2 into the "in" position directs light from the sample beam (when the sample shutter is open and the reference shutter is closed) and reference beam (when the reference shutter is open and the sample shutter is closed) through the associated window W-6 and onto the mirror M-9 which focuses the light onto the entrance slit of the second spectral region spectrometer 1216, where it is dispersed and collected by its detector.

Data from the third spectral region is collected in a similar fashion by flipping "in" the third spectral region source flip-in mirror FM-3 and the third spectral region detector flip-in mirror FM-4, while flipping "out" the second spectral region source flip-in mirror FM-1 and the second spectral region detector flip-in mirror FM-2.

Once the sample and reference measurements for each of the spectral regions have been performed a processor (not shown) can be used to calculate the referenced reflectance spectra in each of the three regions. Finally, these individual reflectance spectra are combined to generate a single reflectance spectrum encompassing the three spectral regions.

When operated in a parallel mode, the source and detector flip-in mirrors are replaced with appropriate beam splitters so that data from all three spectral regions are recorded simultaneously.

Just as supplementary light sources could readily be added to the reflectometer of FIG. 12, specific VUV sources could also be integrated with the common optical module for the purposes of system and/or sample cleaning in situations where it is deemed desirable. For example, in one alternative a supplementary VUV light source may be utilized for system and/or sample cleaning. Such a supplementary VUV light source may be a light source that is of a higher intensity then the primary VUV light source. Such a supplementary VUV source may also be a single wavelength line source or have other wavelength characteristics that differ from the primary VUV light source. Use of a high intensity light source may improve the cleaning throughput. In one embodiment relating to the use of a supplementary VUV light source, it may be desirable to configure such source such that light from the source is directed towards mirror M-1 via flip-in mirrors, shutters or the like (not shown). This would allow cleaning of the mirror M-1. In such a configuration the supplemental light source would encounter most if not all of the elements of the optical path of the primary VUV light source utilized for making sample measurements. It will be recognized that the benefits of the techniques disclosed herein may be achieved without encountering all of elements of the optical path of the primary VUV light source although it may be desirable to encounter a substantial number of such elements. Further, it will be recognized that if a supplementary VUV light source is utilized, it will be desirable to couple such light source to the system in a manner that the path of such light is contained in an environmentally controlled optical path.

The systems of FIG. 11 and FIG. 12 may be utilized as stand-alone tools or may be integrated with another process tool. In one embodiment, the systems of FIG. 11 and FIG. 12 may be merely attached to a process tool with some mechanism that allows for transport of the sample between the process tool and the metrology tool sample chamber. In another alternative, the sample chamber may be constructed in a manner that it shared within the process tool such that the metrology tool and the process tool may be more tightly integrated together. For example the instrumentation/optics chamber may communicate with a sample chamber that is formed with a process tool through the use of a window, gate valve or other coupling mechanism. In this manner the sample need not need not leave the environment of the process tool, rather the sample may be contained within a region of the process tool such as a processing chamber, a transport region or other region within the process tool.

As is evident the system presented in FIG. 11 and FIG. 12 contains exemplary components to facilitate the environmental monitoring methodology outlined in FIG. 1, the system contaminant monitoring methodology outlined in FIG. 7 and the contaminated sample measurement methodology presented in FIG. 9. In general all three effects (i.e. accumulation of absorbing species within the instrumental volume, contamination of optical surfaces within the instrument and sample contamination) can significantly influence optical data in the VUV and hence, it may be desirable to simultaneously employ all three methodologies in order to achieve optimum system performance from instruments operating in this spectral region. The operational flowchart 1300 presented in FIG. 13 provides an example of how this may be accomplished.

First the volume of the instrument is evacuated to a pre-determined pressure at step 1305. Next, the instrument is backfilled with a non-absorbing gas to a pre-determined measurement pressure 1310. Once the measurement pressure has been attained the system is prepared for measurement using the system contaminant monitoring methodology outlined in FIG. 7 as indicated at step 1315. Thus, at step 1315 the various system contaminant steps 710-760 of FIG. 7 may be performed. Once the state of the system is deemed stable and "clean" at step 1315, the intensity spectrum from the reference sample is immediately obtained at step 1320 for time $t_1$. The concentrations of absorbing species are presumed to be at their lowest achievable level at this point in time. The intensity spectrum obtained at this time may be utilized as part of the environmental monitoring process corresponding to step 130 of FIG. 1. Measurements on test samples may then be performed for some pre-determined time period at step 1325 utilizing the contaminated sample measurement methodology outlined in FIG. 9 steps 910-970.

Once the pre-determined measurement time has elapsed, the state of the controlled environment is assessed again at step 1330 by preparing the system for measurement utilizing the system contaminant monitoring methodology outlined in FIG. 7. Performing the system contaminant monitoring and cleaning steps again may place the various optical surfaces in a similar state as they were at step 1315. This allows the completion of the environmental monitoring steps under a condition that more accurately matches the system condition for the first intensity measurement recorded at step 1320. Thus, after step 1330, the intensity spectrum from the reference sample is again recorded at time $t_2$ as indicated at step 1335. The ratio of the two intensity spectra (time $t_1$ and time $t_2$) from the reference sample is then calculated and analyzed in steps 1340 and 1345 in order to determine the concentrations of absorbing species $N_1$, $N_2$, etc. At step 1350, the determined concentrations are then compared to threshold values in order to determine whether or not the environment in the instrument is suitable to support further measurements. If the environment is deemed suitable (i.e. the determined concentrations are less than the threshold values), then further measurements may be conducted once the system is again prepared for measurement via the process of FIG. 7 as indicated by step 1355. Conversely, if as indicated by step 1360 the environment is found to be inadequate to support further measurements the environment may be regenerated by reinitiating the procedure of FIG. 13 by returning control to step 1305. Thus, steps 1335-1360 correspond to the environmental monitoring steps 150-195 of FIG. 1.

Figure 13:
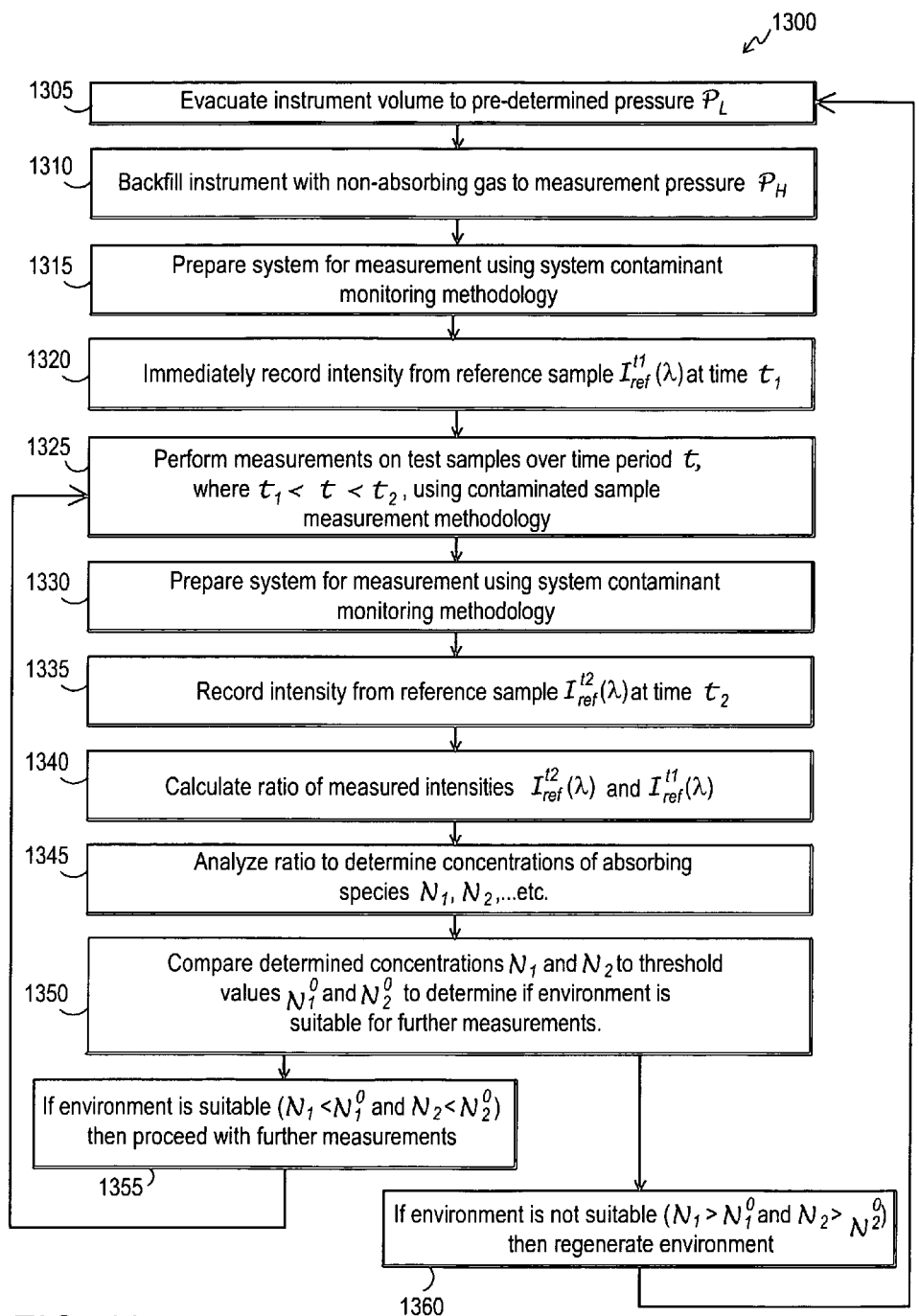
FIG. 13 is an exemplary operational flowchart for a VUV optical metrology instrument.

As shown in FIG. 13, the various concepts of the environmental monitoring and regeneration of FIG. 1, the system contaminant monitoring and cleaning of FIG. 7 and the sample cleaning of FIG. 9 may all be integrated together for use in controlling an optical metrology tool. It will be recognized that the ordering of the various techniques may be changed and that FIG. 13 is merely illustrative of one way of combining the various concepts. For example, the concepts may be implemented serially rather than integrating the steps together as shown in the technique of FIG. 13. Moreover, the concepts need not all be utilized together. For example, in alternative embodiments only one or two of the concepts may be utilized.

The extent to which contamination effects (both environmental and surface/sample) will degrade the performance of VUV optical metrology instrumentation will generally depend on a wide range of factors including, but not limited to, tool design, method of operation, measurement frequency, sample load methodology, and sample characteristics. As a result, it is expected that the operational procedure outlined in FIG. 13 may be modified on a case by case basis in order to ensure optimum instrument performance is maintained.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as presently preferred embodiments. Equivalent elements may be substituted for those illustrated and describe herein and certain features of the invention may be utilized independently of the use of other features, all as would be apparent to one skilled in the art after having the benefit of this description of the invention.

What is claimed is:

1. A method of controlling an atmosphere in an optical metrology tool comprising:
   providing at least a first environmentally controlled chamber and a second environmentally controlled chamber, the first and second environmentally controlled chambers configured for passage of a light beam having wavelengths below DUV wavelengths;
   lowering the concentration of an optical absorbing species in at least one of the first and second environmentally controlled chambers by utilizing vacuum evacuation techniques, the at least one of the first and second environmentally controlled chambers being a controlled atmosphere chamber;
   backfilling, with a non-absorbing gas, the controlled atmosphere chamber so as to improve optical performance by increasing a pressure within the controlled atmosphere chamber above a vacuum evacuation pressure level; and
   transmitting the light beam having wavelengths below DUV wavelengths while the controlled atmosphere chamber is in the backfilled state.

2. The method of claim 1, wherein the optical performance is improved by increasing optical transmission.

3. The method of claim 2, wherein the optical transmission is increased by suppressing absorbed species from outgassing from surfaces of the optical tool.

4. The method of claim 1, wherein the optical performance is improved by decreasing contaminant migration.

5. The method of claim 4, wherein decreasing contaminant migration limits the degradation of reflective properties of optical surfaces that results from contaminants adhering to the optical surfaces.

6. The method of claim 4, wherein the optical performance is also improved by increasing optical transmission.

7. The method of claim 1, wherein the first chamber is a sample chamber and second chamber is an optics chamber, the lowering of the concentration of an optical absorbing species and the backfilling being done in the sample chamber.

8. The method of claim 1, wherein the optical metrology tool is a stand alone optical metrology tool.

9. The method of claim 1, wherein the first chamber is a sample chamber and second chamber is an optics chamber, the lowering of the concentration of an optical absorbing species and the backfilling being done in the optics chamber.

10. The method of claim 9, wherein the sample chamber is integrated within a processing tool.

11. The method of claim 1, wherein the first chamber is a sample chamber and second chamber is an optics chamber, the lowering of the concentration of an optical absorbing species and the backfilling being done in both the optics chamber and the sample chamber.

12. The method of claim 1, wherein the optical absorbing species is moisture or oxygen.

13. The method of claim 1, wherein the vacuum evacuation pressure level is less than $1\times10^{-5}$ Torr.

14. The method of claim 1, further comprising applying energy to the optical absorbing species during the lowering step.

15. The method of claim 1, wherein the energy is applied through mechanical, thermal or radiative methods.

16. The method of claim 1, wherein the backfilling increases the pressure within the controlled atmosphere chamber to a range of 300-700 Torr.

17. The method of claim 1, further comprising continuing to provide a purge gas to the controlled atmosphere chamber after the backfilling step.

18. The method of claim 1, further comprising adding trace levels of a gas to the controlled atmosphere chamber.

19. The method of claim 18, wherein the trace levels of gas promote surface cleaning processes.

20. A method of controlling an atmosphere in an optical metrology tool comprising:
providing at least an environmentally controlled sample chamber and an environmentally controlled optics chamber, the sample chamber and optics chamber each being configured for passage of a light beam having wavelengths below DUV wavelengths;
decreasing from an ambient state the concentration of moisture or oxygen in at least one of the sample chamber and the optics chamber by utilizing vacuum evacuation techniques, the at least one of the sample chamber and the optics chamber in which the decreasing occurs being a controlled atmosphere chamber;
backfilling, with a VUV non-absorbing gas, the controlled atmosphere chamber so as to decrease contaminant migration by increasing a pressure within the controlled atmosphere chamber above a vacuum evacuation pressure level; and
transmitting the light beam having wavelengths below DUV wavelengths while the controlled atmosphere chamber is in the backfilled state.

21. The method of claim 20, wherein decreasing contaminant migration limits the degradation of reflective properties of optical surfaces that results from contaminants adhering to the optical surfaces.

22. The method of claim 21, wherein the decreasing of the concentration of moisture or oxygen and the backfilling being done in the sample chamber.

23. The method of claim 21, wherein the optical metrology tool is a stand alone optical metrology tool.

24. The method of claim 21, wherein the decreasing of the concentration of moisture or oxygen and the backfilling being done in the optics chamber.

25. The method of claim 24, wherein the sample chamber is integrated within a processing tool.

26. The method of claim 21, the decreasing of the concentration of moisture or oxygen and the backfilling being done in both the optics chamber and the sample chamber.

27. The method of claim 20, further comprising continuing to provide a purge gas to the controlled atmosphere chamber after the backfilling step.

28. The method of claim 21, further comprising adding trace levels of a gas to the controlled atmosphere chamber.

29. The method of claim 21, wherein the trace levels of gas promote surface cleaning processes.

30. A method of controlling an atmosphere in an optical metrology tool comprising:
providing at least an environmentally controlled sample chamber and an environmentally controlled optics chamber, the sample chamber and optics chamber each being configured for passage of a light beam having wavelengths below DUV wavelengths;
providing a sample beam optical path and a reference beam optical path, the optical path lengths of the sample beam optical path and the reference beam optical patch being matched;
decreasing from an ambient state the concentration of moisture or oxygen in at least one of the sample chamber and the optics chamber by utilizing vacuum evacuation techniques, the at least one of the sample chamber and the optics chamber in which the decreasing occurs being a controlled atmosphere chamber;
backfilling, with a VUV non-absorbing gas, the controlled atmosphere chamber so as to improve the optical performance by increasing a pressure within the controlled atmosphere chamber above a vacuum evacuation pressure level; and
transmitting the light beam having wavelengths below DUV wavelengths while the controlled atmosphere chamber is in the backfilled state.

31. The method of claim 30 wherein the optical performance is improved by increasing optical transmission.

32. The method of claim 31, wherein the optical transmission is increased by suppressing absorbed species from outgassing from surfaces of the optical tool.

33. The method of claim 30, wherein the optical performance is improved by decreasing contaminant migration.

34. The method of claim 33, wherein decreasing contaminant migration limits the degradation of reflective properties of optical surfaces that results from contaminants adhering to the optical surfaces.

35. The method of claim 33, wherein the optical performance is also improved by increasing optical transmission.

36. A method of determining an environmental contamination state in an optical metrology tool comprising:
obtaining a first intensity measurement from a reference sample at a first time;
obtaining a second intensity measurement from the reference sample at a second time;
analyzing the first and second intensity measurements;
determining from the analyzing of the first and second intensity measurements if the environmental contamination state of the optical metrology tool is suitable for further use based upon variations between the first intensity and the second intensity; and adjusting the environment of the optical metrology tool if the environmental contamination state of the optical metrology tool is determined to be unsuitable for further use.

37. The method of claim 36, further comprising performing a first evacuation and backfill operation of at least one environmentally controlled chamber of the optical metrology tool prior to obtaining the first intensity measurement.

38. The method of claim 36, wherein the first and second intensity measurements include intensity spectrum which include at least in part wavelengths below DUV wavelengths.

39. The method of claim 36, wherein the adjusting the environment comprises performing an evacuation and backfill operation of at least one environmentally controlled chamber of the optical metrology tool.

40. The method of claim 39, wherein the evacuation and backfill operation comprises:
configuring the first environmentally controlled chamber for passage of a light beam having wavelengths below DUV wavelengths;
lowering the concentration of an optical absorbing species in the first environmentally controlled chamber by utilizing vacuum evacuation techniques;
backfilling, with a non-absorbing gas, the first environmentally controlled chamber so as to improve optical performance by increasing a pressure within the first environmentally controlled chamber above a vacuum evacuation pressure level; and
transmitting the light beam having wavelengths below DUV wavelengths while the first environmentally controlled chamber is in the backfilled state.

41. The method of claim 39, further comprising performing an initial evacuation and backfill operation of the at least one environmentally controlled chamber of the optical metrology tool prior to obtaining the first intensity measurement.

42. The method of claim 36, wherein concentrations of absorbing species are determined for at least the second time.

43. The method of claim 36, wherein the variations between the first intensity measurement and the second intensity measurement are analyzed by calculating a ratio of the first and second intensity measurements.

44. A method of determining an environmental contamination state in an optical metrology tool comprising:
obtaining a first intensity measurement from a reference sample at a first time;
obtaining a second intensity measurement from the reference sample at a second time;
analyzing the first and second intensity measurements; and
determining from the analyzing of the first and second intensity measurements if the environmental contamination state of the optical metrology tool is suitable for further use based upon variations between the first intensity and the second intensity;
wherein the variations between the first intensity measurement and the second intensity measurement are analyzed by calculating a ratio of the first and second intensity measurements; and
wherein measured concentrations of the absorbing species are determined at the first time and the second time.

45. The method of claim 44, wherein the determination regarding the environment is based upon comparing at least the measured concentration of the absorbing species at the second time to a threshold value for the absorbing species.

46. The method of claim 36, wherein a plurality of the optical components utilized to obtain the first intensity spectrum measurement and the second intensity spectrum measurement are also utilized for making sample measurements with the optical metrology tool.

47. The method of claim 36, wherein at least a plurality of optical components utilized to obtain the first intensity spectrum measurement and the second intensity spectrum measurement are dedicated monitoring components.

48. The method of claim 36, wherein the optical metrology tool comprises a reference optical path and a sample optical path.

49. The method of claim 48, wherein the reference optical path optically matches a sample optical path.

50. A method of determining an environmental contamination state in an optical metrology tool that operates at wavelengths that at least include wavelengths below DUV wavelengths, the method comprising:
obtaining a first intensity spectrum measurement from a reference sample at a first time, the first intensity spectrum measurement comprising at least a plurality of wavelengths below DUV wavelengths;
obtaining a second intensity measurement from the reference sample at a second time, the first intensity spectrum measurement comprising at least a plurality of wavelengths below DUV wavelengths;
analyzing the first and second intensity measurements;
determining from the analyzing of the first and second intensity measurements if the environmental contamination state of the optical metrology tool is suitable for further use based upon variations between the first intensity and the second intensity.

51. The method of claim 50, wherein a plurality of the optical components utilized to obtain the first intensity spectrum measurement and the second intensity spectrum measurement are also utilized for making sample measurements with the optical metrology tool.

52. The method of claim 50, wherein at least a plurality of optical components utilized to obtain the first intensity spectrum measurement and the second intensity spectrum measurement are dedicated monitoring components.

53. The method of claim 50, wherein the optical metrology tool comprises a reference optical path and a sample optical path.

54. The method of claim 53, wherein the reference optical path optically matches a sample optical path.

55. The method of claim 50, further comprising performing a first evacuation and backfill operation of at least one environmentally controlled chamber of the optical metrology tool prior to obtaining the first intensity measurement.

56. The method of claim 55, further comprising adjusting the environment of the optical metrology tool if the environmental contamination state of the optical metrology tool is determined to be unsuitable for further use.

57. The method of claim 56, wherein the adjusting the environment comprises performing a second evacuation and backfill operation of at least one environmentally controlled chamber of the optical metrology tool.

58. The method of claim 50, further comprising adjusting the environment of the optical metrology tool if the environmental contamination state of the optical metrology tool is determined to be unsuitable for further use.

59. The method of claim 58, wherein the adjusting the environment comprises performing an evacuation and backfill operation of at least one environmentally controlled chamber of the optical metrology tool.

60. The method of claim 59, wherein the backfill operation comprises adding trace levels of a gas to the environmentally controlled chamber.

61. The method of claim 60, wherein the trace levels of gas promote surface cleaning processes.

62. The method of claim 18, wherein the gas comprises oxygen.

63. The method of claim 19, wherein the gas comprises oxygen.

64. The method of claim 28, wherein the gas comprises oxygen.

65. The method of claim 29, wherein the gas comprises oxygen.

66. The method of claim 60, wherein the gas comprises oxygen.

67. The method of claim 61, wherein the gas comprises oxygen.

* * * * *

UNITED STATES PATENT AND TRADEMARK OFFICE
CERTIFICATE OF CORRECTION

PATENT NO. : 7,622,310 B2  Page 1 of 1
APPLICATION NO. : 11/600414
DATED : November 24, 2009
INVENTOR(S) : Harrison et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 187 days.

Signed and Sealed this

Twenty-sixth Day of October, 2010

David J. Kappos
*Director of the United States Patent and Trademark Office*